United States Patent [19]
Siiman et al.

[11] Patent Number: 5,776,706
[45] Date of Patent: Jul. 7, 1998

[54] POLYMERIC PARTICLES HAVING A BIODEGRADABLE GELATIN OR AMINODEXTRAN COATING AND PROCESSES FOR MAKING SAME

[75] Inventors: Olavi Siiman, Davie; Alexander Burshteyn, Hialeah; Ravinder K. Gupta, Pembroke Pines, all of Fla.

[73] Assignee: Coulter Corporation, Miami, Fla.

[21] Appl. No.: 813,022

[22] Filed: Mar. 6, 1997

Related U.S. Application Data

[62] Division of Ser. No. 336,725, Nov. 9, 1994, Pat. No. 5,639,620, which is a continuation of Ser. No. 961,157, Oct. 15, 1992, abandoned, which is a continuation-in-part of Ser. No. 607,253, Oct. 31, 1990, Pat. No. 5,169,754.

[51] Int. Cl.$^6$ ............ G01N 33/569; G01N 33/545; G01N 33/553

[52] U.S. Cl. ............ 435/7.21; 427/2.11; 427/2.13; 427/2.14; 427/127; 427/128; 427/129; 427/130; 427/131; 427/213.35; 427/215; 427/216; 427/337; 428/403; 428/407; 435/5; 436/518; 436/524; 436/525; 436/526; 436/529; 436/531; 436/532; 436/533

[58] Field of Search ............ 427/2.11, 2.13, 427/2.14, 127–131, 213.35, 215.216, 337, 338; 428/403, 407; 435/5, 7.21; 436/518, 524, 525, 526, 529, 531, 532, 533, 534

[56] References Cited

U.S. PATENT DOCUMENTS

| | | | |
|---|---|---|---|
| 3,639,558 | 2/1972 | Cszimas | 424/12 |
| 3,970,518 | 7/1976 | Giaever | 436/526 |
| 4,010,038 | 3/1977 | Iwasaki et al. | 424/492 |
| 4,210,418 | 7/1980 | Brown et al. | 422/58 |
| 4,253,844 | 3/1981 | Limet et al. | 435/177 |
| 4,264,766 | 4/1981 | Fisher | 536/51 |
| 4,267,234 | 5/1981 | Rembaum | 428/407 |
| 4,358,388 | 11/1982 | Daniel et al. | 252/62.54 |
| 4,452,773 | 6/1984 | Molday | 436/526 |
| 4,478,946 | 10/1984 | Van der Merwe et al. | 436/518 |
| 4,554,088 | 11/1985 | Whitehead et al. | 436/526 |
| 4,582,622 | 4/1986 | Ikeda et al. | 436/526 |
| 4,738,932 | 4/1988 | Yabusaki | 436/511 |
| 4,783,336 | 11/1988 | Margel et al. | 424/462 |
| 4,795,698 | 1/1989 | Owen et al. | 435/4 |
| 4,849,210 | 7/1989 | Widder | 436/173 |
| 4,891,324 | 1/1990 | Pease et al. | 436/533 |
| 5,200,270 | 4/1993 | Ishida et al. | 436/526 |

*Primary Examiner*—Christopher L. Chin
*Attorney, Agent, or Firm*—Michelle A. Kaye

[57] ABSTRACT

Gelatin and aminodextran coated polymer core particles useful in immunoassays and methods of making the same are disclosed. The preparation of aminodextrans having varying amounts of amine groups is also described, as is a method of crosslinking gelatin and aminodextran without the use of a stabilizer.

9 Claims, 1 Drawing Sheet

POLYMERIC PARTICLES HAVING A BIODEGRADABLE GELATIN OR AMINODEXTRAN COATING AND PROCESSES FOR MAKING SAME

This is a Divisional of application Ser. No. 08/336,725 filed Nov. 9, 1994, now U.S. Pat. No. 5,689,620, which is a Continuation of Ser. No. 07/961,157 filed on Oct. 15, 1992 now abandoned, which is a Continuation-In-Part of Ser. No. 07/607,253, filed Oct. 2/1990 now U.S. Pat. 5,169,754.

RELATED INVENTIONS

This application is related to the following copending applications: Ser. No. 07/827,347, filed Jan. 29, 1992, entitled FORMATION OF COLLOIDAL METAL DISPERSIONS USING AMINODEXTRANS AS REDUCTANTS AND PROTECTIVE AGENTS; and Ser. No. 07/777,467, filed Oct. 17, 1991 as a continuation of Ser. No. 07/255,773, filed Oct. 11, 1986 (now abandoned), entitled IMMUNOREACTANT CARRIERS HAVING A NOVEL BIOCOMPATIBLE COATING AND PROCESS OF MAKING SAME. This application is also related to U.S. Pat. No. 5,062,991 which issued on Nov. 5, 1991. The specifications of the copending patent applications and U.S. Pat. No. 5,062,991 are incorporated herein by reference. The copending patent applications and U.S. Pat. No. 5,062,991 are owned by a common assignee.

FIELD OF THE INVENTION

This invention relates generally to colloidal sized particles having a crosslinked gelatin or aminodextran coating with pendent functional groups attached thereto. Specifically, this invention relates to polymeric colloidal particles having a crosslinked gelatin or aminodextran coating that is functionalized to bind a pendent protein such as an antibody, to methods of making such particles and to the use of such particles in biological assays.

BACKGROUND OF THE INVENTION

The use of polymeric particles and magnetic particles to bind a compound has long been known and used in industrial and laboratory procedures. For example, the Merrifield resins, crosslinked styrene-divinylbenzene spheroidal beads, were among the earliest and most widely used modern substrate particles. They were used in organic synthesis, for heterogenizing homogeneous catalysts and in biochemical reactions. Since the Merrifield resins were fairly large, they could easily be separated by filtration. In some fields, however, it is desirable to use colloidal size particles because the material to be bound is scarce, expensive or is to be used in a procedure wherein larger size particles are not desirable. This is particularly true in the biochemical field.

When particles are of colloidal size, however, their separation from liquid medium by filtration can become lengthy and difficult. In particular, colloidal particles tend to coat the surface of the filter and slow the filtration process. The use of magnetic particles, specifically magnetic particles having a polymeric coating, has found great utility because such particles can be magnetically gathered to one side of a reaction vessel and the bulk of the reaction medium simply decanted. The word "particles" as used herein encompasses spheres, spheroids, beads and other shapes as well and is used interchangeably with such terms unless otherwise specified.

The use of coated magnetic particles has found a particular utility in biological applications, especially where antibodies are bound to the surface coating of the particles. The bound antibodies may be used to capture a specific biological substance from a test sample containing numerous biological samples or to capture undesired species from the test sample, leaving the desired species in the sample.

The categories of coated magnetic particles also known as magnetic spheres or beads, can be divided into four general classes.

1. Core-and-shell beads with a magnetic core and a hard shell coating of polymerized monomer or a silanizing agent. See U.S. Pat. No. 4,267,234 to Rembaum (polyglutaraldehyde shell around ferrofluid core particles); U.S. Pat. No. 4,454,234 to Czerlinski (suspension or emulsion polymerized coating around submicron magnetic particles); U.S. Pat. No. 4,554,088 to Whitehead et al. (silanized magnetic oxide particles of polydisperse size and shape); and U.S. Pat. No. 4,783,336 to Margel et al. (suspension polymerized polyacrolein around ferrofluid particles).

2. Core-and-shell beads with a magnetic core and a loose shell of random coil or globular polymer which may or may not be crosslinked. See U.S. Pat. No. 4,452,773 to Molday (dextran coating around ferrofluid particles) and U.S. Pat. No. 4,795,698 to Owen et al. (protein such as bovine serum albumin around ferrofluid particles.

3. Magnetic latex materials formed by uniformly embedding ferrofluid particles in polystyrene latex particles. See U.S. Pat. No. 4,358,388 to Daniel et al.

4. Porous polymer particles filled with magnetic materials such as polymer-ferrite or polymer maghemite composite systems. See K. Nustad et al. "Monodisperse Polymer Particles In Immunoassays And Cell Separation", Microspheres: Medical and Biological Applications, A. Rembaum and Z. Tökes, eds. (Boca Raton, Fla.: CRC Press, 1988) pages 53–75; C. D. Platsoucas et al., "The Use Of Magnetic Monosized Polymer Particles For The Removal Of T Cells From Human Bone Marrow Cell Suspensions", ibid. at pages 89–99; and International Patent Publication No. WO 83/03920, Ughelstad et al. (polymer coated magnetic particles prepared by treating compact or porous particles with a solution of iron salts and the use of such particles for medical, diagnostic or other purposes).

The usefulness of most polymer coated magnetic beads in medical and biological applications has been limited by practical considerations such as the uniformity of particle size and shape, the need for the biological reagent to be strongly bound to the particle, a preference for hydrophilic polymer coatings as opposed to hydrophobic coatings, and whether or not the coating is biodegradable. While biodegradability is of particular importance where a biological reagent is to administered in vivo, it is also important in various cell sorting, separation and assay procedures. The most desirable coated magnetic particles would have the following features.

1. The particles should be as small as possible in order to maximize the surface area on which the biological reagent is coated, but the particles should still be easily separable with a small magnet. Small size and large surface area are desirable in order to use the least possible quantity of particles to remove the targeted substance; e.g., to interact with on the order of $10^6$ cells per sample in one step, thereby avoiding sequential additions and work-ups.

2. There should be a low non-specific binding of the antibody-coated particles to cell surfaces. The particle surface should be hydrophilic or covered with a coating of a hydrophilic substance to which the antibody is attached.

3. The polymer and antibody layers on the particles should be covalently bound to each other in order to reduce dissociation and conformational changes.
4. The coating on the magnetic particles and any molecular chains which link an antibody to the polymer surface should be metabolizable.
5. In positive selection of cells, a mechanism for quickly and easily recovering viable cells from the magnetic particles should be available in order that recovered cells can be cultured.
6. In the negative selection of cells, the antibody-coated particles should be sterile so that the remaining cells can be cultured.

In addition to magnetic particles, there is also a need for polystyrene latex (PSL) particles which have been coated with hydrophilic polymer coatings to which antibodies can be subsequently bound. These polymer coated PSL particles can be used in bead-based cell population analyses and immunoassays. However, non-magnetic PSL particles, as made, usually have a relatively low density of various functional groups such as carboxyl or amino groups. Consequently, covalent coupling of coating materials such as dextran or gelatin to the surface of PSL particles is not satisfactory.

The various particles described above have been used in the biological arts to immobilize a variety of biological substances, particularly antibodies. In using such particles, immobilization of antibodies by covalent coupling is preferred to immobilization by antibody adsorption which requires careful and separate adjustment of pH and antibody concentration for each monoclonal antibody used. P. Bagchi et al., J. Colloid Interface Sci., 83: 460–478 (1981); J. Lyklema, Colloids and Surfaces, 10: 33–42 (1984); M. D. Bale et al., J. Colloid Interface Sci., 125: 516–525 (1988); C. C. Ho et al., ibid., 121: 564–570 (1988); "Proteins at Interfaces: Physicochemical and Biochemical Studies", ACS Symposium Series, No. 343, J. L. Brash and T. A. Horbett, Eds. (Washington: Amer. Chem. Soc., 1987); W. Norde, Adv. Coll. Interface Sci., 25: 267–340 (1986); A. V. Elgersma et al., Abstracts of the 198th Amer. Chem. Soc. Meeting, Miami Beach, Fla., Sept. 10–15, 1989, COLL 0131; and D. E. Brooks, Annenberg Center for Health Sciences and H. B. Wallis Research Facility at Eisenhower Latex Conference, Orlando, Fla., Dec. 4–5, 1989. However, even when the pH and antibody are carefully controlled, there is little assurance that the orientation of adsorbed antibody will be such that an active adsorbed antibody will result. Adsorbed antibodies also have long term storage problems arising from antibody desorption from the particles' surfaces. Furthermore, proteins, such as antibodies, tend to achieve maximum adsorption on hydrophobic surfaces at or near the pI of the protein. However, if electrostatic interactions between charge groups are important, then the adsorbing surface and the adsorbate should have net opposite charges. Covalent coupling methods, on the other hand, are not as sensitive to these conditions.

Covalent coupling methods have been used with particles of magnetite embedded in carboxy-modified latex subsequently coated with aminodextran (R. S. Molday et al., FEBS Lett. 170: 232–238 (1984)) and derivitized with a number of antibodies as described in co-pending application Ser. No. 07/977,467. If the antibody is of IgG isotype, the covalent coupling method assures that the linkage between the antibody and the particles occurs at the antibody Fc or hinge region, and not at the antibody's Fab region. If the antibody is of pentameric IgM isotype which has only Fab regions exposed, the coupling of one Fab region to the particle will still leave four Fab regions exposed and available for reaction.

This invention provides for the preparation of magnetic and non-magnetic particles having a biodegradable coating to which can be attached-pendent biological substances, such as monoclonal antibodies. The particles of the invention can be used in various cell separation and assay methodologies. Biodegradability in the coating used on the magnetic or latex core material is important in cell separation technology. For example, antibodies may be conjugated to gelatin coated magnetic particles such as manganese ferrite particles. These particles would thus contain a proteinaceous coating and a manganese-iron oxide core, all of which are biodegradable. In a positive cell selection procedure using such particles, once the desired cell has been isolated from other cells, the particles and coating can be allowed to degrade in a manner such that the cells are kept viable and can be cultured for further use. Alternatively, the enzyme collagenase can be used first to release the core material (magnetic or latex) by digestion of the gelatin coating. The core material can then be removed from the cell suspension before culturing the cells. In the negative selection of cells with such biodegradable beads, the beads can be left in the cell suspension from which targeted cells were removed without compromising the viability of the remaining cells. For example, in bone marrow purging operations using biodegradable magnetic beads, there is less concern about leaving behind some beads in the purged marrow that is to be transplanted in a patient. Currently, synthetic polymer-magnetite particles prepared by Ughelstad et al. International Patent Publication No. WO 83/03920, and conjugated with antibody are being used in bone marrow purging. The polymer is not biodegradable and imparts a hydrophobic surface to these beads. This hydrophobicity, which is not present in the gelatin coated particles of the claimed invention, is responsible for non-specific interactions between the beads and cells. As a result of this non-specific interaction, the selectivity is poor and more beads must be used to attain the desired level of treatment. The claimed invention avoids these problems.

Gelatin coated particles have been found to have some problems regarding non-specific interactions with certain cells, notably platelets [Clinical Hematology, 8th ed., M. M. Wintrobe et al., Eds (Lea & Febiger, Philadelphia, Pa. 1981), Chapter 16] and phagocite cells such as monocytes [Basic & Clinical Immunology, 6th ed., D. P. Stites et al., Eds. (Appleton & Lange, East Norwalk, Conn. 1987), Chapter 9]. The problem arises because the amino acid sequence of gelatin (as exemplified by the α-1 chain of rat and calf skin collagen) includes three regions with the tripeptide sequence Arg-Gly-Asp (RGD) [The Theory of the Photographic Process, 4th ed., T. H. James ed. (Mac Millan, New York 1977) Chapter 2, page 54] which duplicates the RGD binding sequence of fibronectin, a component of the extracellular matrix that specifically promotes cellular adhesion [Biochem. Biophys. Res. Comm 170: 1236 (1990)]. Those biological cells with fibronectin expressed on their surface have a specific affinity for collagen which is equivalent to crosslinked gelatin. For example, the antibody conjugated, gelatin coated magnetic ferrite particles used in the separation of subsets of white blood cells will also bind to the fibronectin that is present on the surface of platelets and monocytes. The result is the non-specific depletion of cells from a sample because monocytes and platelets, as well as cells which contain the antibody-specific antigen, will bind to the gelatin coated particles. The non-specific cell depletion can be substantially overcome by using an aminodextran as the outermost particle coating layer.

SUMMARY OF THE INVENTION

The invention provides discrete colloidal particles having a core of a polymeric substance having a hydrophobic surface coated with a water soluble gelatin or an aminodextran. The polymeric core is a non-gelatin, non-aminodextran core selected from the group consisting of polymeric materials or substances which have covalently attached surface amine-reactive groups and polymeric substances which do not have surface amine-reactive groups. A plurality of pendent functional groups is attached to the coated particles. The pendent functional may be or have within their structure terminal aldehyde or carboxylate groups, amine groups, sulfhydryl groups or maleimidyl groups, and polyclonal or monoclonal antibodies.

The invention provides discrete colloidal particles having pendent biological functional groups such as polyclonal and monoclonal antibodies covalently attached to the crosslinked gelatin or aminodextran coating by means of a heterobifunctional agent, for example, a short diamine or polyamine chain, so as to enable advantageous use of said antibody functionalized particles in biological separations and assays. The heterobifunctional agent acts as a bridging group between the biological substance or functional group and the crosslinked gelatin or aminodextran.

The invention further provides a method for the preparation of colloidal particles having a solid core of polymeric material having a hydrophobic surface coated with a water soluble gelatin or an aminodextran, each having a plurality of functional groups. The process, in general, comprises the coating of a solid core polymeric material which has a hydrophobic surface with gelatin or aminodextran without the formation of covalent bonds between the gelatin or aminodextran and the polymeric material or coupling the amino groups of an aminodextran to reactive groups on the surface of the polymeric material (for example, aldehyde or carboxylic acid or acid ester groups on the surface of polystyrene particles), crosslinking the adsorbed gelatin or aminodextran or the coupled aminodextran and derivatizing the crosslinked gelatin or aminodextran to obtain a product having a desired reactive species covalently bound to said crosslinked gelatin or aminodextran surface. Though it is preferred to crosslink the aminodextran coupled to the surface of the polymeric beads, such crosslinking is not necessary in all situations. For example, if the biological material under assay or reagents used in the assay do not interact with the polymeric material, crosslinking may not be required. The invention further provides a process for the preparation of particle bound polyclonal and monoclonal antibodies from the gelatin and aminodextran coated particles, and for the use of such particles in biological assays, particularly immunological assays.

The invention also provides a process for the separation, either positive or negative, and analysis of biological substances comprising contacting a solution containing a biological substance with an antibody covalently bound to the surface of a crosslinked gelatin or aminodextran coated solid core particle, incubating the resultant mixture at a temperature and for a time sufficient to form a complex between said antibody and said substance, analyzing the resulting particle containing solution to determine particle-shifted light scatter or other particle-shifted properties. If desired, the particles may also be separated from the solution and either or both analyzed independently analysis performed.

DETAILED DESCRIPTION OF THE INVENTION

Figure 1:
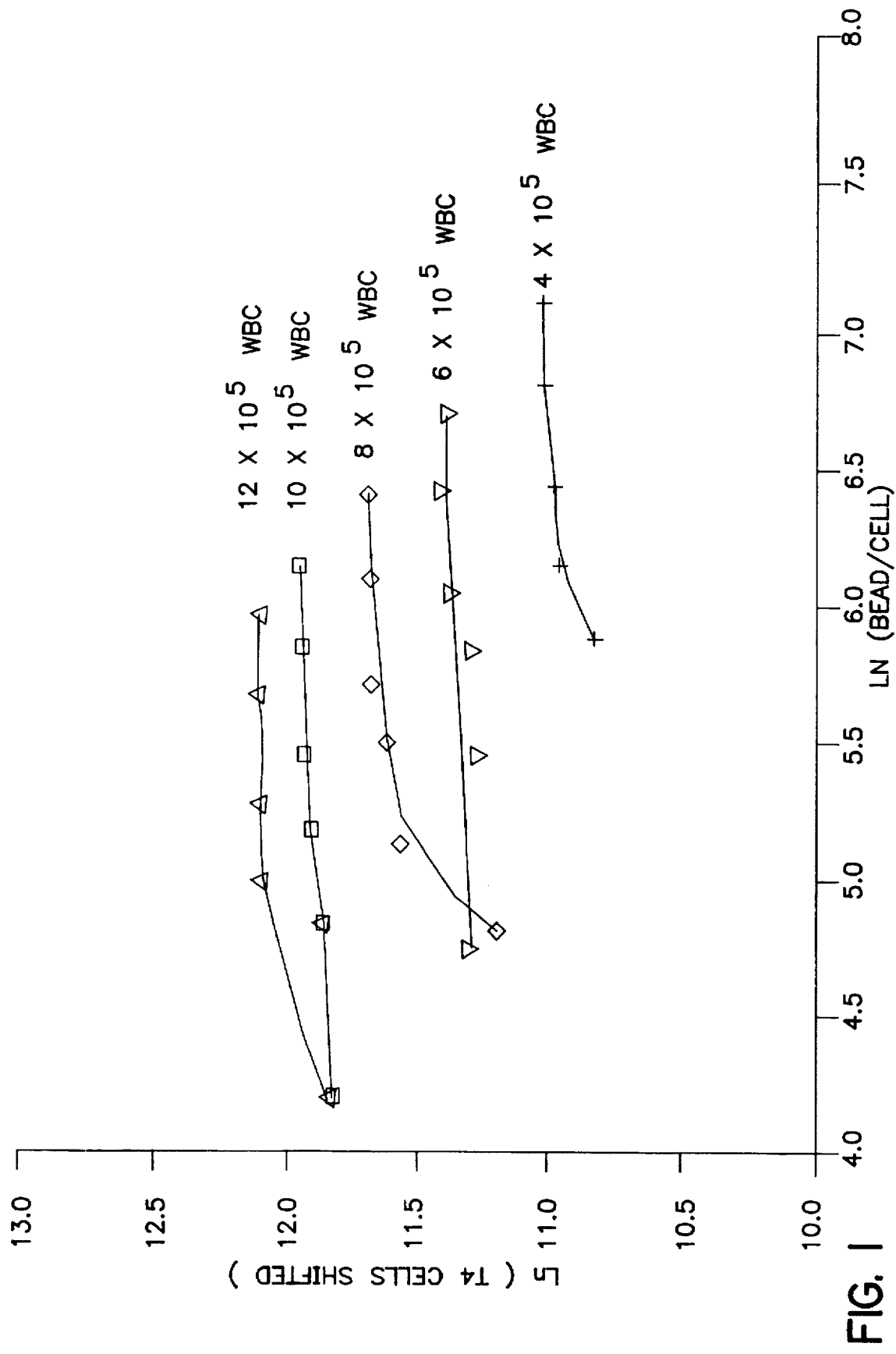
FIG. 1 represents the T4 population shift analysis by T4-antibody, aminodextran coated polystyrene beads as carried out in Example 5.

In the Detailed Description Of The Invention and Preferred Embodiments which follow, applicants place reactive maleimidyl groups on the crosslinked gelatin or aminodextran coated particles and reactive sulfhydryl groups on the antibodies. These may be reversed such that the maleimidyl groups are attached to the antibodies and the sulfhydryl groups are attached to the crosslinked gelatin. Applicants have also elected to use 2-iminothiolane hydrochloride as the model for the sulfhydryl reagent and sulfo-SMCC (described below) as the model for the maleimidyl reagent. Other reagents enumerated or of like nature and result may also be used.

The aldehyde/sulfate polystyrene latex and sulfated polystyrene latex particles used herein represent two different types of particles. The former has reactive aldehyde groups which can combine with a substance such as an aminodextran and form covalent bonds. The latter lacks such reactive groups. A coating substance is adsorbed onto the surface of sulfated polystyrene particles without: the formation of covalent bonds between the adsorbed substances and the particles surface. In addition to polystyrene latex, other, polymeric materials may be used as core particles. For example, polyacrylate, polymethacrylate, polyester, and polyphylene oxide particles, among others, may coated with gelatin or an aminodextran and derivatized as described herein. However, the availability and cost of these other polymeric particles makes the use of polystyrene particles preferred. Other considerations which favor polystyrene are uniformity in the size and shape of the particles which are to be coated. The size of the polymer particles ranges from about 0.1 to about 5.0 microns. The preferred particle size is in the range of about 0.1 to 1.0 microns.

Lastly, the choice of whether or not an aminodextran coating is crosslinked is dependent on two factors. The first is whether or not the aminodextran is conjugated to the polymeric particles surface as it would if, for example, it were coated onto carboxylated beads. If the aminodextran is not conjugated, then the coating must be crosslinked. The second factor is the practioner's choice. If the aminodextran coating is conjugated, then the practioner is free to crosslink the coating or not crosslink it. In general, if a "relatively thick" aminodextran coating is desired, the aminodextran layer conjugated to the polymer surface is crosslinked and additional aminodextran is used to block unreacted crosslinking agent reactive groups. Subsequent reactions are carried out as described herein. The aminodextran/crosslinking agent reactions can be carried out a plurality of times, if so desired. If only a single aminodextran layer is desired, then the layer conjugated to the surface can be further derivatived, without crosslinking, as described herein, or the layer can be crosslinked and unreacted crosslinking agent reactive groups can be blocked by reaction with polyamines such as ethylenediamine and triethylenediamine, among others. These particles may then be further derivatized as also described herein.

Glossary of Biological Reagents

All reference to the monoclonal antibodies (mAb) used herein is by the identifying designations used by Coulter Corporation, Hialeah, Florida for monoclonal antibodies made by Coulter Corporation. The following information further identifies the antibodies used herein. The use of these monoclonal antibodies is by way of example only and is not to be understood as limiting the invention. The term "CD"

refers to "Cluster Designation" adopted by the International Workshops on Human Leukocyte Differentiation Antigens. A.T.C.C. is the American Type Culture Collection, Rockville, Md.

| Antibody | CD | Description or Reference |
|---|---|---|
| T11 | CD2 | Derived from hybridization of mouse NS/1-AG4 cells with spleen cells of BALB/cJ mice immunized with T cell chronic, lymphocytic leukemia cells. |
| T4 | CD4 | As T11, but immunized with peripheral human T lymphocytes. |
| T8 | CD8 | As T11, but immunized with human thymocytes. |
| KC-16 | — | U.S. Pat. No. 4,752,563; A.T.C.C. Deposit No. CRL 8994. |
| 1D3 | — | U.S. Pat. No. 4,931,395; A.T.C.C. Deposit No. HB 9445 |
| KC-48 | — | U.S. Pat. No. 4,865,971; A.T.C.C. Deposit No. HB 9584 |
| MO2 | CD14 | R.F. Todd et al, J. Immunol., 126:1435 (1981). |
| PLT-1 | CD41 | R.F. Todd et al., Blood, 59:775 (1982); Griffith et al., Blood, 61:85 (1983). |
| KC-56 | CD45 | Derived from the hybridization of mouse Sp2/0-AG14 myeloma cells with spleen cells from BALB/c mice immunized with a derivative of the CEM cell line |
| B4 | CD19 | L.M. Nadler et al., J. Immunol. 134: 2228 (1985). |

Other reagents used herein and commercially obtainable from Coulter Corporation are:

MsIgG1-RD1/MsIgG1-FITC: Mouse IgG1-phycoerythrin [RD1]/Mouse IgG1-Fluorescein Isothiocyanate [FITC].

T11-RD1/B4-FITC: Ab T11-phycoerythrin/Ab B4-FITC.

T4-RD1/T8-FITC: Ab T4-phycoerythrin/Ab T8-FITC.

1X PBS: Dissolve 53.8 g $K_2HPO_4$ in 1.6 L distilled water. Add 12.8 g $KH_2PO_4$ and stir until dissolved. Then dissolve 340 g NaCl in the solution. After all salts dissolved, add distilled water to make up to 2 L volume and filter through a 0.2 μm filter. The resulting solution is 20X PBS. 1X PBS is prepared by dilution of 1 part 20X PBS with 19 parts distilled water. The 1X PBS solution has a pH in the range of 7.1–7.3, typically 7.2, and is 0.15M in NaCl.

DETAILED DESCRIPTION

In using the method of the invention, uniform particles (the core material) in the size range of 0.1 to 5.0 microns are coated with gelatin or an aminodextran, and the coating is fixed by means of a chemical fixing agent or is chemically bound to the particle surface. The uncoated particles have a hydrophobic or partially hydrophobic surface. The preferred size of the particles is in the range of 0.1 to 1.0 microns.

The magnetic particles used in the claimed invention may be preformed magnetic particles that are dispersible in a gelatin solution or they may be magnetic particles prepared by the in situ use of gelatin in the preparation of said magnetic particles. The in situ method for the preparation of monodispersed colloidal particles of ferrites of manganese, zinc, mixed manganese-zinc, iron, barium, cobalt and nickel involves the use of an aqueous metal hydroxide gel first formed by mixing ferrous and other metal salts in an aqueous gelatin solution with potassium or sodium hydroxide and potassium or sodium nitrate solution, all solutions being purged with nitrogen gas. The conversion of the gel to the metal oxide sol is achieved by mild thermal treatment at 90° C. (low temperature) for 4–72 hours, during which nitrate oxidation of ferrous iron occurs. The magnetic particles in the hydrosol are then washed and resuspended in a 1% aqueous solution of gelatin of the type described below prior to further treatment as described herein. In preparing magnetic particles using in situ gelatin as described herein, only one type of gelatin has been found optimal for such use. This is type B or alkali-cured gelatin with a pI range of 4.75 to 5.0. The procedures for the preparation of magnetic particles using in situ gelatin are fully described in copending application Ser. No. 07/532,434, filed Jun. 4, 1990, now U.S. Pat. No. 5,062,991, the teachings of which is incorporated here by reference, and also described herein. The gelatins which are crosslinked according to the present invention are given below.

Gelatin is obtained from highly crosslinked collagen in fibrous tissue, such as skin or bone, which has been acid or base cured and then thermally degraded at or above 39° C. The collagen molecule combines the helical structure of the α-type proteins with the inter-chain hydrogen bonding of the β-type proteins. The three collagen peptide chains, each in the form of a left handed helix, are twisted about each other to form a superhelix. Upon treatment, the three peptide strands of the superhelix are separated by the breaking of inter-chain hydrogen bonds and replacing them with hydrogen bonds to water molecules. The separated peptides have random coil configurations ["The Theory of the Photographic Process", T. H. James,Ed., (New York: MacMillan Press, 1977)]. The α-1 peptide chain has been sequenced and found to have over 1000 residues [D. J. S. Hulmes et al., J. Mol. Biol., 79:137 (1973)]. They contain extensive segments of mainly non-polar residues; and the polar residues which are present are not localized into acidic or basic regions. Furthermore, in contrast to globular proteins which tend to expose their hydrophilic residues on their surfaces and bury their hydrophobic residues within their structure {see R. E. Dickerson et al., "The Structure and Action of Proteins", (Menlo Park: Benjamin, 1969)}, random coil gelatin has exposed hydrophobic residues readily available for adsorption onto the surface of hydrophobic particles such as polystyrene latex particles or magnetite and ferrite particles. When aqueous gelatin is adsorbed onto the surface of a particle, its hydrophilic side chains (aspartyl, glutamyl and lysyl residues) tend to be directed externally to the aqueous medium. The lysyl groups, which function as the intramolecular crosslinkage points in collagen, will be accessible for cross linking in the adsorbed gelatin. Glutaraldehyde is frequently used as the crosslinking agent. U.S. Pat. No. 4,478,946 to Van Der Merwe et al. and S. B. Sato et al., J. Biochem., 100: 1481–1492 (1986).

A number of different, usually bifunctional, crosslinking agents such as bis [2-(succinimidooxycarbonyloxy)-ethyl] sulfone, disuccinimidyl tartarate, ethylene glycol bis (succinimidylsuccinate), disuccinimidyl suberate and glutaraldehyde may be used in the claimed invention. Glutaraldehyde, the preferred gelatin or aminodextran crosslinking agent, as commercially available, contains mainly monomer absorbing at 280 nm (nanometers). However, there is present in the commercial product a significant amount of polymeric material which gives rise to an absorbance at 235 nm. The polymeric species, probably trimers or linear oligomers, are of sufficient length to form intra-and inter-molecular bridges between amino groups present on the adsorbed gelatin. By judiciously selecting the reaction time between the adsorbed gelatin or aminodextran and glutaraldehyde, the gelatin can be suitably fixed on the core particles so that it will not be removed during subsequent separation, reaction and washing steps. Large flocs created by excessive crosslinking of free gelatin can thereby be avoided and interparticle crosslinking is negated.

Several types of gelatin are available for use in the present invention, such as type A, acid cured, isoelectric point pH 8.3–8.5 and type B, alkali cured, isoelectric point, pH 4.75–5.0. Each type is available in a variety of Bloom Numbers which indicate gel strength. Type A gelatin Bloom Numbers useful in the claimed invention range from 60 to 300. Type B Bloom Numbers useful in the claimed invention range from 60 to 225. The type A, 175 Bloom gelatin used in the preferred embodiment of the claimed invention is preferred and was selected for its relatively large number of lysyl residues and its lower Bloom number in order to minimize intermolecular interactions between gelatin molecules. For optimum adsorption on magnetite and ferrite particles, it was buffered to pH 8.4, the middle of its isoelectric point range, at which pH it is most soluble in water and gives the least viscous solution. The instability of gelatin adsorbed on ferrite particles, which instability arises when glutaraldehyde is added, was overcome by the present invention by the use of more dilute particle and gelatin concentrations [0.1% weight/volume (w/v) instead of the 2.5% w/v solids suspension that was used in other reactions herein] in conjunction with an inert polymeric stabilizer, polyvinylpyrrolidone (PVP), that does not react with glutaraldehyde. The use of the stabilizer and the 25-fold lower gelatin concentrations avoids interparticle crosslinking during the glutaraldehyde fixation reaction. Since polymer desorption is a very slow process relative to the time of the glutaraldehyde fixation reaction, approximately 6 minutes, a stable gelatin coating around the core particle was produced.

In order to be useful in the biological and medical arts, the fixed (crosslinked) gelatin coating should contain functional groups which can be conjugated with biologically active substances such as antibodies to produce immobilized biologically active substances attached to the particle surface. Covalent coupling of biological substances to the particle surface is preferred over simple adsorption. The coupling of an antibody, either polyclonal or monoclonal, to the crosslinked gelatin surface is accomplished by the use of "short chain" diamines or polyamines and a heterobifunctional reagent. (Hereafter, the word polyamine includes diamines). The polyamine is reacted with residual aldehyde or carboxylate groups, either naturally occurring or present by the steps of this invention, present on the crosslinked gelatin surface. The use of polyamine serves not only to block aldehyde/carboxylate groups, but also serves to replenish gelatin amino groups such as lysyl amino groups which were depleted during the crosslinking process. This procedure is generally accomplished in two steps. In the first step, unreacted terminal aldehyde groups are reacted with a polyamine followed by sodium borohydride ($NaBH_4$) reduction of the resulting Schiff's base to create stable, saturated C—N linkages. In the second step, exposed carboxylic acid residues (glutamic, aspartic) of gelatin are coupled to polyamine in the presence of a water soluble carbodiimide such as 1-ethyl-3-(3-dimethylaminopropyl)-carbodiimide (EDAC).

Short chain polyamines, including diamines, are preferred in order to avoid crosslinking neighboring aldehyde or carboxylic acid groups on the same particle or to avoid linking such groups on different particles. One polyamine amine group reacts with the gelatin surface and the other(s) remains unreacted and available for coupling, directly or indirectly, to a biological substance. Examples of 'short chain' polyamines include ethylenediamine, phenylenediamine, propylenediamine, 1,4-cyclohexanediamine, cyclohexenediamine, tetramethylenediamine, diethylenetriamine, 1,5-diamino-3-(2-aminoethyl)pentane $|(H_2NCH_2CH_2)_3C|$ and other polyamines of general formulas $H_2NCH_2$—$(CH_2)_x$—$CH_y$ $(CH_3)_z$—$NH_2$ and $C_6H_{4+a}(NH_2)_2$ where x=0–3, y=1 or 2 and Z=1 when y=1 or Z=0 when y=2, and a=0 or 6. Ethylenediamine is preferred.

The coupling of the biological substance to the particle involves activation of the free amino groups of the gelatin-coated particles with a water soluble heterobifunctional reagent such as 2-iminothiolane hydrochloride (IT), sulfosuccinimidyl-4-(N-maleimidomethyl)cyclohexane-1-carboxylate (sulfo-SMCC), m-maleimidobenzoyl-N-hydroxysuccinimide ester, N-succinimidyl-3-(2-pyridyldithio)propionate, succinimidyl-4-(p-maleimidophenyl)butyrate, N-succinimidyl-(4-iodoacetyl) aminobenzoate, the reagents listed above as substitutes for glutaraldehyde and the like. The 2-iminothiolane hydrochloride and the maleimidyl/succinimidyl reagents are preferred. E.Ishikawa, Immunoassay Supp., 1:1–16 (1980) and J. Immunoassay, 4:209–227 (1983); M. Imagawa et al., J. Appl. Biochem., 4: 41–57 (1982); and M. D. Partis, J. Protein Chem., 2: 263–277 (1983). When using sulfo-SMCC, the active sulfosuccinimidyl ester end of sulfo-SMCC will react at pH 7.0–7.5 with amines to give peptide bonds. The sulfo-SMCC/diamine bridging unit which results is approximately 16 Angstroms in length.

When performing the polyamine and sulfo-SMCC reactions, particle aggregation was monitored by microscopic examination (1000×magnification) and by light scattering analysis using a Coulter N4MD submicron particle size analyzer (Coulter Corporation, Hialeah, Fla.), or similar instrument.

The maleimidyl group of sulfo-SMCC will react at pH 6.5–7.5 with free sulfhydryl groups to form a stable, covalent thioether bond. However, it is essential that the coated particles with which sulfo-SMCC is reacted contain no free sulfhydryl groups which could react with the maleimidyl end of sulfo-SMCC. Sulfhydryl groups are found on or generated from cystine and cysteine amino acid residues of which gelatin has very few. Consequently, the crosslinked gelatin particles of the claimed invention do not require a protein modifier to block free sulfhydryl groups prior to reaction with sulfo-SMCC.

Biological substances, particularly either monoclonal or polyclonal antibodies, can be covalently linked to the maleimidyl end of sulfo-SMCC functionalized particles by means of sulfhydryl groups present, either naturally or by derivatization, on said biological substances. Biological substances which have cysteinyl residues inherently contain sulfhydryl groups. To introduce additional sulfhydryl groups, the biological substances' amine groups are activated with Traut's reagent, 2-iminothiolane hydrochloride (IT), at a pH in the range of 7–10 [M. Erecinska, Biochem. Biophys. Res. Commun., 76:495–500 (1977); J. M. Lambert et al., Biochemistry, 17: 5406–5416 (1978); and M. E. Birnbaumer et al., Biochem J., 181: 201–213 (1979)]. When the biosubstances are antibodies, antibody lysyl and terminal amine groups are activated by IT. In the present invention, reaction conditions and the concentration of reactants were varied to determine the optimal coupling so that the biosubstance, especially antibody, when conjugated with the substrate particles, retains its maximum functional activity. Although maleimides react quite rapidly with sulfhydryl groups in solution, the same groups immobilized on particles were given longer reaction periods to react with protein. Particle and antibody concentrations during antibody conjugation were optimized to avoid aggregation, particularly when IgM antibodies were used. The procedures optimized for IgM antibodies can be used for all monoclonal antibodies with an isoelectric point range of about 5.0 to about 9.0. Generally, about 30-fold less antibody was required to achieve covalent coupling than is required for simple adsorption; a consequence of importance where expensive or hard to obtain antibodies are involved.

The optimum concentration of iminothiolane-activated antibody to use in conjugation reactions with maleimidyl-activated particles was determined by the use of activated antibody binding curves (Surface Antibody vs Total Antibody Concentration). After a typical conjugation period, a sample is taken and filtered through a 0.2 μm low-protein binding filter. The filtrate is analyzed spectrophotometrically. The surface antibody is determined by the difference between the total antibody in the starting solution and the antibody in the filtrate (Total Antibody - Filtrate Antibody). The binding data in antibody (Ab) concentration dependent runs show Langmuir isotherm-type characteristics; i.e., a linear low concentration region for total antibody versus surface antibody concentration, a smooth inflection point and a plateau indicating saturation at the particle surface at high concentrations. The antibody concentrations actually used were those at the inflection point or at concentrations slightly above the inflection point. Binding constants were obtained graphically by recasting the equation of a hyperbola into one for a straight line. A double reciprocal plot of $1/n_2^s$ versus $1/C_2$ was constructed, where $n_2^s$ is the number of moles of IT-Ab bound per gram of particles and $C_2$ is the molar concentration of free IT-Ab at equilibrium. Linear plots are indicative of Langinuir-type binding behavior. The binding constants $K_1=n^sK$ of IT-Ab for sulfo-SMCC-activated ferrite particles were calculated using the equation $1/n_2^s=1/(n^sKC_2)+1/n^s$, where K is the intrinsic binding constant and $n^s$ is the number of moles of binding sites per gram of ferrite particles. Linear regression analysis of plots for various monoclonal antibodies gave the following results:

Ab T11: $K=1.3\times10^6 M^{-1}$   $n^s=5.9\times10^{-8}$ mol/g
Ab KC16: $K=6.4\times10^6$  "   $n^s=5.1\times10^{-7}$ ""
Ab 1D3: $K=2.7\times10^6$  "   $n^s=2.0\times10^{-7}$ ""
Ab MO2: $K=1.8\times10^7$  "   $n^s=7.1\times10^{-7}$ ""

The results for the ferrite particles compare favorably with similar data for commercially available carboxy-modified latex beads (23% magnetite, 0.980 μm dia., obtained from Rhône-Poulenc) covalently coated with aminodextran and conjugated to monoclonal antibodies and protein. These results are:

Ab T11: $K=6.5\times10^5 M^{-1}$   $n^s=1.1\times10^{-7}$ mol/g
Ab KC16: $K=3.2\times10^6$  "   $n^s=6.9\times10^{-8}$ ""
Ab 1D3: $K=3.2\times10^5$  "   $n^s=1.7\times10^{-7}$ ""
Ab MO2: $K=2.0\times10^6$  "   $n^s=1.6\times10^{-7}$ ""
Ab KC48: $K=2.5\times10^5$  "   $n^s=7.6\times10^{-8}$ ""
Ab PLT-1: $K=2.8\times10^5$  "   $n^s=2.2\times10^{-7}$ ""
Streptavidin:
$K=1.3\times10^6$  "   $n^s=9.5\times10^{-8}$ ""

In addition to ferrite core beads, the present invention was also evaluated using monoclonal antibodies conjugated to crosslinked gelatin-coated polystyrene beads. The binding constants for these antibodies, which compare favorably to both evaluations given above, are:

Ab T8: $K=1.7\times10^6 M^{-1}$   $n^s=9.5\times10^{-8}$ mol/g
Ab T4: $K=2.5\times10^7$  "   $n^s=3.5\times10^{-8}$ ""

The results with the polystyrene beads indicate that the method of the present invention is not limited to magnetic spheres, but may be used with any colloidal particles that have a hydrophobic surface.

DESCRIPTION OF THE PREFERRED EMBODIMENT USING MAGNETIC BEADS

Preparation of Magnetite and Other Magnetic Particles in Gelatin Solution 10 mmol (5 ml) of 2M $KNO_3$ solution, 12.5 mmol (2.5 ml) of 5M KOH solution and 11.25 ml of double distilled water (DDW) were mixed and purged with $N_2$ gas for 10 minutes (Solution A). 6.25 mmol (6.25 ml) of 1M $FeSO_4$ solution and 25 ml of freshly prepared, $N_2$ purged, 2% type B, 225 Bloom, bovine skin gelatin solution [useful gelatin solution range is from about 0.8% to about 2.0%)] were then added to Solution A in a Pyrex® bottle, mixed, swept with $N_2$ gas, capped tightly, and placed undisturbed in an oven at 90° C. for 4 hours. After the suspension of black magnetite particles had reached room temperature, they were sonicated for ½ hour, washed with 1% type B, 225 Bloom gelatin solution, and then contacted with a large excess of 1% w/v gelatin as is the next step.

Metal ferrites may also be prepared using gelatin in situ in their preparation. In trials with other metals, namely $Mn^{2+}$, $Zn^{2+}$, $Co^{2+}$, $Ni^{2+}$, and ($M^{2+}$) the molar ratio of $M^{2+}:Fe^{2+}$ was kept at 1:2, but nitrate was used instead of sulfate for $Co^{2+}$ and $Ni^{2+}$. The total metal-to-hydroxide molar ratio was maintained at 1:2; but the relative $KNO_3$ to total metal and $KNO_3$ to KOH molar ratios were altered. In preparing the mixed Mn/Zn ferrite, a 1:1 molar ratio of manganese sulfate to zinc sulfate and the same total molar amount of non-ferrous metal ions were used. The following is an example.

10 mmol (5 ml) of 2M $KNO_3$ solution, 18.75 mmol (3.75 ml) of 5M KOH solution and 6.875 ml DDW were mixed and purged with $N_2$ gas for 10 minutes (Solution C). 6.25 mmol (6.25 ml) 1M $FeSO_4$ solution, 3.125 mmol (3.125 ml) of 1M $Co(NO_3)$ solution and 25 ml of type B, 225 Bloom, bovine skin gelatin solution were mixed and purged with $N_2$ gas for 10 minutes. (Solution D). Solution D was added to Solution C in a Pyrex® bottle, mixed, swept with $N_2$ gas, capped tightly, and placed undisturbed in an oven at 90° C. for 5 hours. After the suspension of brown particles had reached room temperature, they were sonicated for ½ hour, washed with 1% type B, 225 Bloom gelatin solution and then contacted with a large excess of 1% w/v gelatin as in the next step.

Using the methods described above, cobalt and nickel ferrite particles of about 0.1 and 0.2 μm in diameter and of spherical shape were formed in large, loosely-held brown aggregates. Zinc gave low yields of light brown magnetic material of less than 0.2 μm diameter even after 72 hours of heat treatment. Dark brown manganese ferrite particles of uniform, spherical shape and 0.3 μm diameter were obtained as single particles in 83–88% yields. Similar light brown manganese-zinc ferrite particles were produced in 49–55% yield after 72 hours of heat treatment at 90° C. For barium, the procedure was modified since $BaSO_4$ is insoluble in water. (Except for the case where barium is present, the divalent metals may be used as their chlorides or sulfates as well as their nitrates). Thus 6.25 mmol (6.25 ml) of 1M $FeCl_2$ solution, 0.5 mmol (5.0 ml) of 0.1 $Ba(NO_3)_2$ solution and 25 ml of 2% gelatin were mixed and purged with $N_2$ gas for 10 minutes (Solution D). Solution C and the remainder of the ferrite preparation procedure was unchanged except 10 mmol KOH solution (2 ml) was used and the heat treatment was continued for 20 hours. Black barium ferrite particles of uniform non-spherical shape with a 0.2 μm diameter were produced.

Preparation of Gelatin Coated Magnetic Particles

A quantity of magnetic particles, for example, manganese ferrite particles, of uniform size (0.3 μm) and spherical shape and prepared using in situ gelatin according to the procedures described above were contacted with a large excess of 1% w/v, type B, 225 Bloom aqueous gelatin solution. Alternately, preformed (i.e., formed by methods other than the in situ use of gelatin), dispersible magnetic particles, for example, manganese ferrite particles, of uniform size (0.3 μm) and spherical shape were contacted with a large excess of 1% w/v, type B, 225 Bloom gelatin solution at ambient temperature for approximately 60 minutes. The particles (either of the above) were then magnetically separated and washed five times with a 2% w/v, type A, 175 Bloom gelatin solution in 0.2M aqueous sodium chloride, pH 8.4. After washing, the particles were stored at ambient temperatures for up to several months as 2.5% w/v (weight/volume) solids suspension in a 2% w/v aqueous solution of the type A gelatin containing 0.2M sodium chloride, 0.1% w/v sodium azide at pH 8.4. Provided the azide content of the storage solution is maintained, the suspension can be stored for up to about 3 months.

Crosslinking the Adsorbed Gelatin 62.5 μL of 25% aqueous glutaraldehyde (0.156 mmol) solution was added to 120 ml of 1% aqueous polyvinylpyrrolidone (MW=40,000) in 0.2M aqueous sodium chloride, pH 7.2. To this, 5 ml of the 2.5% solid suspension prepared above was added to the glutaraldehyde solution and the resulting suspension was mixed at ambient temperature for a time in the range of 3–15 minutes, preferably about 6 minutes.

Blocking of Unreacted Aldehyde Groups 0.105 ml of 99% ethylenediamine (1.56 mmol) was added to a 125 ml suspension of the fixed, gelatin coated magnetic particles (0.1% w/v solids) in 1% PVP solution, 0.2M in sodium chloride, pH 7.2. The resulting suspension was mixed for a time in the range of about 1 to 4 hours, preferably about 2 hours, in a 250 ml tissue culture flask. At the end of the mixing time, 1.25 ml of a 10 mg/ml solution of sodium borohydride ($NaBH_4$) in 0.1 mM KOH was added to the magnetic particles and the resulting suspension was mixed for an additional 15 minutes. The particles were then magnetically separated and washed a plurality, preferably three, times with 0.2M aqueous sodium chloride.

Crosslinking the Adsorbed Gelatin Without the use of Polyvinylpyrrolidone as a Stabilizer 5 ml of 2.5% w/v solids manganese ferrite particles suspended in 2% w/v type A, 175 Bloom gelatin in 0.1M phosphate buffer, pH 8.4, which were prepared as described above were magnetically separated. The clear supernatant liquid was discarded and the residue of magnetic particles was resuspended in 5 ml of 3 mg/ml glutaraldehyde solution prepared by mixing 56 μL of 25% aqueous glutaraldehyde solution with 5 ml of 1 mM aqueous potassium hydroxide, pH 10.00. The resulting suspension of magnetic particles was mixed, preferably roller mixed, for about 30 minutes, washed three times using magnetic separation and resuspended in 5 ml of 1 mM aqueous potassium hydroxide.

For elemental analysis, a 5 ml suspension of the crosslinked gelatin on manganese ferrite particles was further washed fifteen times (15) with distilled water and the magnetically separated residue was dried at 100° C. in an oven. Analysis in weight percent was: Mn, 19.05%; Fe, 49.49%; C, 0.54%, H<0.5%; O, 30.92% by difference. The percentage carbon by weight in gelatin can be obtained from its amino acid content which gives: C, 50.46%; H, 6.765%; N, 18.27; O, 24.29% and S, 0.21%. [See "The Theory of the Photographic Process", 4th Ed., T. H. James, ed. (Macmillan, New York 1977), Chapter 2, page 52]. Thus, for 1 gram of ferrite-gelating particles, there will be 1 g×0.0054/0.5056=0.01070 gram gelatin and 0.9893 gram ferrite. The volume per particle of spherical 0.29 μm diameter manganese ferrite particles is $1.277 \times 10^{-14}$ $cm^3$. Using a particle density of 4.24 $g/cm^3$, the mass per particle is $5.414 \times 10^{-14}$ gram and the number of particles in 0.9893 gram ferrite is $1.827 \times 10^{13}$. Thus, the mass of gelatin per particle is $5.856 \times 10^{-16}$ gram. Assuming a density of gelatin coating of 0.02 $g/cm^3$ from the 2% w/v gelatin before crosslinking with glutaraldehyde, the volume of gelatin per particle is $2.92 \times 10^{-5}$ $cm^3$. Thus the total volume (ferrite and gelatin) per particle is $4.205 \times 10^{-14}$ $cm^3$ and the radius of a sphere consisting of ferrite and gelatin is $2.157 \times 10^{-5}$ cm or 0.2157 μm. The thickness of the gelatin coating is then 0.2157 μm–0.145 μm (mean radius of ferrite particle)=0.0707 μm (i.e., about 71 nm). This value for the thickness of gelatin coating is in good agreement with the following adsorption data for gelatin on various surfaces as obtained from the following publications.

1. A. T. Kudish et al., Proteins at Interfaces, ACS Symposium Series 343, T. L. Brash and T. A. Horbett eds. (Washington, D.C.; American Chemical Society 1987). Chapter 17, pages 261–277: Type A, pig skin gelating on glass gave a coating thickness of 750 Å (0.075 μm) and Type B, calf skin gelatin on glass gave a coating thickness of 500 Å (0.050 μm).

2. N. Kawaniski et al., J. Phys. Chem. 94: 4611–4617 (1970): Type B gelatin, Bloom 259 on mica gave a force versus distance (between mica surfaces) attractive minimum at 75 nm (750 Å).

3. H. Meltger et al., J. Colloid Interface Sci. 126: 292–303 (1988): Denatured, soluble calf skin collagen (i.e., gelatin) on glass gave film thickness of 600–700 Å (0.06000–0.0700 μm).

Reaction with Fixed Gelatin's Carboxylate Residues 2.11 ml of 99% ethylenediamine were added to an 118 ml suspension of the aldehyde-blocked beads, 0.1% w/v solids, in 0.2M aqueous NaCl. The resulting suspension was physically and sonically mixed for approximately 15 minutes. After this mixing, 4.5 ml of 10 mg/ml EDAC in 0.2M NaCl was added and the suspension was first physically and sonically mixed for approximately 15 minutes, and finally physically mixed for a time in the range of about 8–16 hours. The contents of the flask were then magnetically separated, washed a plurality of times with 1X PBS, sonically mixed in 1X PBS for approximately 30 minutes, and finally concentrated to 5 ml of 2.5% w/v solids in 1X PBS. For large scale (100×) preparations, the previous aldehyde blocking step and the EDAC coupling step have been combined to avoid multiple separations and washings. The combination of steps did not result in any loss of activity in the final antibody-conjugated beads.

Activation of Diamine Treated Particles with Sulfo-SMCC

In general, 27 μL of freshly prepared 10 mg/ml sulfo-SMCC in 1X PBS was used per milliliter of 2.5% w/v magnetic particle suspension. In a typical preparation, 135 μL of the sulfo-SMCC solution was added to 5 ml of 2.5% w/v particles. The mixture was then roller mixed in a 15 ml plastic centrifuge tube for approximately one hour, sonically mixed for approximately 5 minutes, magnetically separated, and washed a plurality of times with 1X PBS.

The functionalized, crosslinked, gelatin coated particles resulting from the above series of steps have pendent maleimidyl groups and are suitable for a variety of medical and/or biological uses. If the substance which is desired to be conjugated to the particles has a sufficiency of active sulfhydryl groups, activation of that substance is not necessary, and the following step may be skipped.

Antibody Activation with 2-Iminothiolane Hydrochloride

A 51.24 mg/ml concentrate of T11 monoclonal antibody in 1X PBS containing 0.1% $NaN_3$ was prepared. For 10 mg of T11 antibody and 15 mg/ml antibody concentration during coupling, the total reaction volume should be 0.667 ml. Using a 15:1::IT:T11 activation ratio, 0.9375 µmol (0.129 mg) IT (65 µL of 2mg/ml IT) in 1X PBS is required. Therefore, 0.407 ml of 1X PBS solution was added to 0.195 ml of T11 concentrate, to which resulting solution an additional 65 µL of 2mg/ml IT solution was added. The net resulting solution was roller mixed in a tube reactor for 1 hour. The content of the reaction tube was then applied to the top of a 20 ml G-50 Sephadex column, equilibrated and washed with 100 ml 1X PBS. The derivatized antibody was eluted using 1X PBS and a plurality of 2.5 ml fractions were collected with the aid of a UV monitor. Fractions in the middle of the band absorbing at 280 nm were pooled and the $A_{280}$ value was used to determine T11/IT antibody concentration. Typically, the T11/IT concentration was about 3.0 mg/ml. The T11/IT solution may be concentrated by solvent removal.

Conjugation of T11/IT with Sulfo-SMCC Derivatized Particles

In a laboratory scale conjugation, total volume 5 ml, the concentration of particles was 2.5% w/v solids and the T11/IT concentration was 0.9 mg/ml. In one sample, when the purified T11/IT solution concentration was 1.850 mg/ml, then 2.392 ml of T11/IT antibody solution in 1X PBS was added to 5 ml of 2.5% w/v solids sulfo-SMCC activated particles which had been preconcentrated by the removal of 2.432 ml of supernatant. The T11/IT solution was added to the particles in 0.5 ml increments with sonic and rapid physical mixing between additions. The resultant solution was then roller mixed in a 15 ml tube for approximately two hours. A 1 ml test sample was then taken, filtered through a low-protein binding 0.2 µm filter, and the filtrate analyzed spectrophotometrically for T11 antibody by measuring the absorbance at 280 nm; $A_{280}$ = c (supernatant)=0.3986 mg/ml. [measurement by difference, c (surface)=c (total)–c (supernatant)]. Thus c (surface)=0.9 mg/ml–0.3986 mg/ml= 0.501 mg/ml. This translates to a T11 surface loading of 20 mg T11 per gram particles or, for a specific surface area of 4.89 $m^2$/g for manganese ferrite particles, a 4.1 mg T11/$m^2$ particle surface area. Similar procedures with 2- and 3-fold dilutions of particle concentration, but the same total antibody concentration during conjugation, gave higher surface antibody loading. However, a limitation was reached when a 4-fold dilution of the particles concentration did not yield higher surface coverage of antibody.

Blocking Unreacted Maleimidyl and Sulfhydryl Groups

Unreacted maleimidyl groups on the sulfo-SMCC activated particles were blocked with L-cysteine after antibody conjugation. Typically, 0.480 ml of 5 mg/ml L-cysteine in 1X PBS was added to remaining 4 ml of the conjugation mixture of the previous step and the resulting solution was roller mixed for 15 minutes. Unreacted sulfhydryl groups were blocked by the addition of 0.534 ml of 20mg/ml iodoacetamide in 1X PBS followed by the addition of 0.100 ml of 1M, pH 9.8 sodium borate buffer solution. The resulting solution was roller mixed for 30 minutes, the blocked conjugation mixture was magnetically separate and the particles washed three times with 1X PBS containing 1% bovine serum albumin (fraction V, heat shock) and 0.1% $NaN_3$ (BSA buffer solution). After washing, 4 ml of the foregoing BSA solution was added to the particles, the particles roller mixed for approximately 1 hour, stored at 4° C. for a time in the range of about 8–16 hours, magnetically separated and washed three additional times with BSA buffer.

Antibody containing particles prepared according to the method described herein have been found useful in various cell separation assays. The biological substances used in assays utilizing the invention may be selected from the groups consisting of normal or non-normal T-cells, B-cells, leukocytes, viruses, erythrocytes, cells of the breast, uterus, colon, kidney, liver, lung, testes, stomach, thyroid and parathyroid, and the like; provided that the biological substance contains an antigenic determinant capable of binding to an antibody.

In an embodiment of the invention equivalent to the magnetic particle embodiment described above, the maleimidyl groups and the sulfhydryl groups are transposed. That is, the crosslinked gelatin coated particles are derivatized to have pendent groups ending in reactive sulfhydryl groups in place of the maleimidyl groups described above and the antibodies are derivatized to have reactive maleimidyl groups in place of the sulfhydryl groups described above. The methods used to prepare this equivalent embodiment are the same as described above. In both cases, the antibody is connected to the gelatin surface by a molecular bridge prepared as described.

The following examples are given to illustrate the utility of the claimed invention and are not to be taken as limiting said invention.

EXAMPLE 1

Protocol for Magnetic Bead Depletion of T-cell and B-cell Populations

Mononuclear cells (MNC) were obtained from whole blood-samples by density isolation on Ficoll-hypaque gradients and washed in PBS. $1 \times 10^6$ MNC in 1 ml PBS were added to a series of tubes containing 5, 10, 25, 50 and 100 µL of the monoclonal antibody (MoAb) conjugated magnetic particle suspension (2.5% w/v) being tested. Two tubes were set up for each depletion and for the undepleted control. The resulting suspensions were then nutated for 3 minutes in a multitube vortexer or a single tube nutator. At the end of incubation, the cell suspension was placed for a total of 2 minutes in the magnetic field provided by a single tube magnetic rack. At the end of the magnetic separation, unbound cells were extracted by withdrawing all the clear liquid from the center of the tube with a Pasteur pipet For T- or B-cells (T11, T3, T4, T8, B1, B4), the cell suspension collected after depletion was compared directly to the original cell suspension prior to particle depletion. The samples, original and depleted, were centrifuged for 5 minutes at 1200 rpm and the supernatant decanted to leave approximately 100 µL of PBS remaining in each tube. One tube of each pair of depletion tubes was then stained with 10 µL CYTO-STAT® MsIgG1-RD1/MsIgG1-FITC reagent (MS) and the other tube was stained with 10 µL CYTO-STAT® T11 -RD1/B4-FITC reagent (for T11, T3, B1 or B4 depletions) or with 10 µL of T4-RD1/T8-FITC reagent (for T4 or T8 depletions) at room temperature for 10 minutes. At the end of incubation, 500 µL of PBS were added to each sample and the samples were analyzed by flow cytometry. The samples were analyzed on the EPICS® Profile using the MBead 2-Color program. (EPICS® and CYTO-STAT® are registered trademarks of Coulter Corporation). As the original sample stained with MS control reagent was being run, it was checked to determine whether the lymphocyte population was fully incorporated in Bitmap 1, and adjustments were made if necessary. The left side of discriminator 2 was set for each fluorescence histogram on the channel which would give <1% positive staining. This was done for each sample stained with MS control reagent and then the corresponding tube stained with specific antibody was analyzed. The data were collected and recorded as the absolute number of positive staining cells in the red and green histograms (T and B or T4 and T8) not percent positive. Test results are summarized below.

EXAMPLE 2

Protocol for Magnetic Bead Depletion of Red Blood Cells (RBC)

100 μL of Na$_4$EDTA-anticoagulated whole blood was placed in a series of reaction tubes. To each tube, 25 to 150 μL of KC-16 conjugated magnetic particles suspension (2.5% w/v) was added and the total volume was adjusted to 250 μL using PBS. The suspensions were nutated for 3–5 minutes in a multitube vortexer or a single tube nutator at low mixing speed. When nutation was completed, 1 ml of PBS was added to each sample tube which was then placed on a magnetic rack for 2–5 minutes. All the supernatant was removed from each tube using a Pasteur pipet and saved in labelled tubes. Samples were analyzed on a Coulter S-plus IV or similar rbc counter as total rbc number/ml whole blood. The positive control was 100 μL whole blood plus 1.150 ml PBS to give 100% rbc count and the negative control was 100 μL whole blood plus 1.150 ml of Batch lyse or similar lysing agent to give 0% rbc count. Percentage of rbc depleted=100%−[(rbc count in sample tube)/(100% rbc count)].

EXAMPLE 3

Protocol for Magnetic Bead Depletion of Leukocytes 100 ml of Na$_4$ EDTA-anticoagulated whole blood were collected, divided among a number of centrifuge tubes and centrifuged at 500 g for 10 minutes. The majority of plasma was removed and the buff colored layer of cells from each tube was removed, pooled together and centrifuged at 500 g for an additional 10 minutes. The buff colored cells and the plasma constitute the leuko-rich whole blood which should have an rbc count no greater than 8.0×10$^9$/ml and a white blood cell (wbc) count of 2–4×10$^7$/ml.

100 μL of leuko-rich whole blood was pipetted into a number of reaction tubes. An amount of 10 to 160 μL of magnetic bead suspension (2.5% w/v) was then pipetted into each tube followed by the addition of 200 μL of 1X PBS. (N.B. Lower titer points with 10 to 40 μL of beads should be run first. Additional beads were added only if endpoint depletion was not obtained at 40 μL). Each tube was nutated for 3–5 minutes at low speed. 2 ml of 1X PBS was then added, the contents of a tube mixed and then magnetically separated for 2 minutes. All supernatant liquid was removed and placed in a duplicate tube which was then centrifuged at 400 g for 5 minutes. The resulting supernatant was then carefully removed by pipette and analyzed.

The leuko-rich or the leuko-depleted whole blood samples were analyzed by the addition of 10 μL of single or dual color antibody preparation designed to discriminate for the depletion of specific cells from a mixture of cells. For example, when T11 -conjugated magnetic beads were used in depletion, T11-B4 dual color was used to discriminate between actual T11+ cell depletion and the non-specific depletion of T11 cells (i.e. B-cells). The mixture was vortexed and incubated for 10 minutes at room temperature in the dark. Controls were isotype control and antibody control with undepleted cells. The tubes were then placed on a Coulter EPICS® Q-prep, or similar instrument, and run on the 35 second lyse mode. After the rbc were lysed and the samples fixed (Q-prep), all samples were analysed on a Coulter EPICS® Profile flow cytometer or similar instrument. This procedure is required to obtain data as actual number of cells per volume of sample. Programs available on Profile were used to analyze lymphocytes and monocyte-myeloid populations.

Summary of Test Results using the Protocols of Examples 1–3

1. In a T11/B4 lymphoid cell assay, the undepleted control gave 97,209 T11+, 18,240 B4+, 19,717 monocyte and 25,381 granulocyte counts. After depletion with 10 μL of 2.5% w/v solids magnetic beads conjugated with T11 antibody, the counts were 15,826, 20,181, 19,954 and 30,972 respectively. Depletion with 20 μL T11 antibody-conjugated beads gave 2,256, 20,989, 20,874 and 31,965 counts; 30 μL gave 1,150, 21,428, 20,697 and 35,362 counts; and 40 μL gave 644, 21,232, 19,817 and 33,935 counts, all respectively.

2. In a T4/T8 lymphoid cell assay, the undepleted control, which contained 4.1×10$^5$ T8 and 7.9×10$^5$ T4 cells, gave 54,415 T4 and 27,906 T8 counts. After depletion with 10, 20 and 30 μL of 2.5% w/v solids magnetic beads conjugated with T8 antibody the counts were 57,030 and 12, 59,538 and 6, and 60,905 and 5, respectively.

3. In an erythrocyte/thrombocyte assay, the undepleted control contained 4.5×10$^6$ wbc, 4.4×10$^8$ rbc and 4.7×10$^7$ platelets. Depletion experiments were conducted using 20, 40, 60 and 80 μL of 2.5% w/v solids magnetic beads conjugated with KC-16 antibody. The wbc, rbc and platelets remaining after depletion were 20 μL: 4.4×10$^6$ wbc, 1.6×10$^8$ rbc and 4.3×10$^7$ platelets; 40 μL: 4.6×10$^6$ wbc, 1×10$^7$ rbc and 4.5×10$^7$ platelets; 60 μL: 4.5×10$^6$ wbc, 1×10$^7$ rbc and 4.3×10$^7$ platelets; and 80 μL: 4.5×10$^6$ wbc, 1×10$^7$ rbc and 4.3×10$^7$ platelets. The results indicate that 40 μL of 2.5% solids beads which contained 1.85×10$^{10}$ particles removed 4.3×10$^8$ rbc, thus giving a particle-to-rbc ratio of 43.

4. In a myeloid cell assay, the undepleted control gave 73,821 lymphocyte, 13,426 monocyte and 55,661 granulocyte counts. Depletion studies were conducted using 10, 20, 30 and 40 μL of 2.5% w/v solids magnetic beads conjugated with KC-48 antibody. The results were 10 μL: 70,330, 9,309 and 340 counts; 20 μL: 68,414, 2,006 and 1,332 counts; 30 μL: 62,966, 1,597, and 922 counts; and 40 μL: 59,340, 1,546 and 899 counts, all respectively.

A similar depletion study was conducted using 10, 20, 30 and 40 μl of 2.5% w/v solids magnetic beads conjugated with 1D3 antibody. The results were 10 μL: 76,405, 13,839 and 1,597 counts; 20 μL: 73,198, 8,653 and 1,216 counts; 30 μL: 65,667, 2,590 and 2,130; and 40 μL: 66,276, 1,906 and 1,686 counts, all respectively.

A further depletion study was conducted using 10, 20 30 and 40 μL of 2.5% w/v solids magnetic beads conjugated with M02 antibody. The results were 10 μL: 72,563, 3,107 and 56,520 counts; 20 μL: 72,905, 3,616 and 34,533 counts; 30 μL: 69,644, 1,618 and 32,313 counts; and 40 μL: 69,477, 1,210 and 30,899 counts, all respectively.

5. In an erythrocyte/thrombocyte assay, the undepleted control contained 7×10$^6$ wbc, 4.9×10$^{10}$ rbc and 3.0×10$^7$ platelets. Depletion studies were conducted using 20, 40, 60 and 80 μL of 2.5% w/v solids magnetic beads conjugated with PLT-1 antibody. The results, after depletion, were 20 μL: $10 \times 10^6$ wbc, $5.4 \times 10^{10}$ rbc and $1 \times 10^6$ platelets; 40 μL: $10 \times 10^6$ wbc, $5.8 \times 10^{10}$ rbc and $1 \times 10^6$ platelets; 60 μL: $7 \times 10^6$ wbc, $5.1 \times 10^{10}$ rbc and $1 \times 10^6$ platelets; and 80 μL: $10 \times 10^6$ wbc, $5.6 \times 10^{10}$ rbc and 0 platelets.

Description of the Preferred Embodiment Using Polystyrene Latex Particles

A. Gelatin Coated Polymeric Particles

Preparation of Gelatin Coated Polystyrene Latex Particles

Sulfated polystyrene latex particles (IDC Corporation, Portland, Oregon) of uniform size (2.17 μL ±3.0%) and spherical shape were used to exemplify the invention and were dispersed in distilled water and centrifuged for 10 minutes at 3000 rpm. The supernatant liquid was discarded and the particles were resuspended in 1% aqueous, type A, 175 Bloom gelatin at 2.5% w/v solids, sonically mixed for 1 minute to aid redispersion and roller mixed for 8–16 hours. The sulfated polystyrene latex particles did not have aminereactive groups attached to the polystyrene. However, polystyrene latex particles with surface amine-reactive groups can be used in the same manner even though gelatin contains few, if any, amine groups. Furthermore, the polystyrene latex particles may have embedded magnetic particles or the particle may consist of a magnetic nucleus having a polymer coating, in this case a coating of polystyrene latex. If such magnetic particles are used, than separations may be done magnetically instead of by centrifugation.

Crosslinking the Adsorbed Gelatin and Blocking Unreacted Aldehyde Groups

A 0.300 ml aliquot of 25% aqueous glutaraldehyde (0.749 mmol) was added to 575 ml phosphate buffered saline (1X PBS) containing 1% polyvinylpyrrolidone (40,000MW). 25 ml of 2.5% w/v solids sulfate polystyrene latex particles in 1% type A, 175 Bloom gelatin solution were then added to the glutaraldehyde solution. The resulting suspension was placed in a 1 L polypropylene centrifuge bottle and roller mixed for 6 minutes. After mixing, 0.505 ml of 99% ethylenediamine (7.49 mmol) was added to the 600 ml of particles in 1X PBS and the resulting suspension was roller mixed for about 2–3 hours. 6.0 ml of 10 mg/ml NaBH$_4$ in 0.1 mM aqueous KOH were added and the suspension again roller mixed for 15 minutes. The particles were washed three times with 0.2M aqueous NaCl by centrifugation and decantation. After washing, the particles were resuspended in 0.2M NaCl to yield 24 ml of 2.5% w/v solids suspension.

Crosslinking the Adsorbed Gelatin Without Polyvinylpyrrolidone Stabilizer

56 μL of 25% aqueous glutaraldehyde solution were mixed with 5 ml of 1 mM aqueous potassium hydroxide. 5 ml of 2.5% w/v solids sulfate polystyrene latex particles suspended in 2% w/v, type A gelatin, 0.1M in phosphate buffer, pH 8.4, were separated by centrifugation and the supernatant liquid was discarded. The separated gelatin coated polystyrene latex particles were suspended in 5 ml of the 3 mg/ml glutaraldehyde solution prepared as described herein. The resulting suspension was mixed, preferably roller mixed, for about thirty minutes. After the glutaraldehyde addition and mixing was completed, 20 μL of ethylenediamine (2:1 diamine-to-glutaraldehyde molar ratio) was added to the reaction mixture which was then stirred for an additional 2–3 hours. Subsequently, 0.313 ml of a 40 mg/ml solution of sodium borohydride (100 mg per gram of beads) in 1 mM KOH was added to the reaction and the resulting mixture stirred for about 10–30 minutes. The crosslinked particles were then separated by centrifugation and washed three times, and resuspended in 5 ml of 0.2M aqueous sodium chloride.

Coupling of Ethylenediamine to the Carboxylate Residues of Gelatin Coated on Polystyrene Latex Particles A 0.404 ml aliquot of 99% ethylenediamine (6.00 mmol) was mixed with 24 ml of fixed, aldehyde blocked, gelatincoated polystyrene particles, 2.5% w/v solids, prepared with or without the use of polyvinylpyrrolidone stabilizer. A 0.960 ml sample of 10 mg/ml EDAC (0.050 mmol) in 0.2M NaCl solution was added to the particles and roller mixed for 8–16 hours in a 50 ml centrifuge tube. The contents of the tube were washed five times with 1X PBS after centrifugation for 10 minutes at 3000 rpm and decantation. The particles were then resuspended in sufficient 1X PBS to give a total volume of 24 ml.

Particle Activation by Sulfo-SMCC and Antibody Coupling to the Gelatin Coated Polystrene Latex Particles The activation of the particles and the coupling of monoclonal antibodies to gelatin coated polystyrene particles was carried out using the same procedures as followed for magnetic beads, except that separation of the particles was accomplished by centrifugation for 10 minutes at 3000 rpm followed by decantation of the supernatant liquid.

EXAMPLE 4

T4 and T8 Cell Population Assays Using Monoclonal Antibody Covalently Bound to Gelatin Coated Polystyrene Latex Particles 15 μL of KC-48-conjugated magnetic bead suspension (2.5% w/v) were added to 50 μL of whole blood. The mixture was gently vortexed for 15 seconds and magnetically separated. 28 μL of the supernatant were transferred to a new test tube and 15 μL of T4- or T8-conjugated, gelatin coated polystyrene latex beads (2.5% w/v) were added to the tube. The contents of the tube were then vortexed for 15 seconds. 300 μL of Batch lyse for red blood cells were added, the mixture vortexed for 4 seconds, 120 μL of a lyse quencher added and the mixture again vortexed for 4 seconds. The resulting sample was analyzed on a Coulter VCS or similar instrument for the population of shifted T-cells. Controls were whole blood and whole blood with granulocytes removed by KC-48-conjugated magnetic beads. The percent of T4 or T8 cells in a sample equals the cell population shifted into the KC-48 depleted region of DC versus opacity. The percent (%) T4 or T8 cells=[(Shifted T4 or T8 cell population)÷(total original lymphocyte population)]×100. The plot from which this percentage is obtained is DC verus [(RF−85)+DC], where RF is the radio frequency scatter, DC is the direct current resistance and −85 is a constant.

In an embodiment of the invention equivalent to the latex particle embodiment described above, the maleimidyl groups and the sulfhydryl groups are transposed. That is, the crosslinked gelatin coated particles are derivatized to have pendent groups ending in reactive sulfhydryl groups in place of the maleimidyl groups described above and the antibodies are derivatized to have reactive maleimidyl groups in place of the sulfhydryl groups described above. The methods used to prepare this equivalent embodiment are the same as described above.

B. Aminodextran Coated Particles

Preparation of Aminodextrans

The specification of copending application Ser. No. 07/827,347, filed Jan. 29, 1992, is incorporated herein by reference; particularly the section therein which teaches the preparation of aminodextran by partial cleavage and oxidation of the glucopyranose rings in dextran to aldehyde functional groups, coupling of the aldehyde groups to a polyamine (preferably a diamine and most preferably 1,3-diaminopropane) to form Schiff base linkages and reduction of the Schiff's base linkages to form stable carbon-nitrogen bonds. The details for both small scale (Method 1) and large scale (Method 2) preparation of aminodextran are given in the copending application. Aminodextrans were prepared therein having average molecular weights of 10,000, 40,000, and 2,000,000 (T-10, T-40 and T-2M) with 1X (1X=3.3% substitution of sugar residues), 2X (6.6%) and 3X (9.9%) molar amounts of amino groups. The 2X- and 3X-aminodextrans were obtained using two and three times the amount of sodium periodate used in the 1X oxidation of aminodextran. The amount of 1,3-diaminopropane used for Schiff base formation was kept constant in copending Ser. No. 07/827,347 because a large excess of 1,3-diaminopropane was used.

It has subsequently been determined that product yield may be increased by using only a ten percent excess of diamine over the stoichiometric 2:1 diamine to periodate, ratio, performing the diamine addition reaction at a temperature in the range of about 5–100C, and spectrophotometrically monitoring the reaction in the near UV region for Schiff's base formation and completion of reaction. These modifications reduce the aminolysis of the polymeric sugar into lower molecular weight fragments and thus increase yields after desalting and concentration by hollow fiber membrane filtration as taught in Ser. No. 07/827,347. This improved method of preparing aminodextrans (Method 3) has also enabled the production of quantities of 5X-aminodextran (16.5% substitution of sugar residues) as follows.

Method 3. Preparation of 5X-Aminodextran

T-2M dextran (50 g, 0.308 mol, obtained from Sigma or Pharmacia) was added to a 1-quart or 1-liter glass blender bowl containing 300 ml of distilled water. The mixture was blended at maximum speed until all the dextran dissolved, typically about 3–5 minutes. A solution of 26.75 g (0.125 mol) of $NaIO_4$ in 300 ml distilled water was added to the dextran solution over about a 10 minute period using vigorous magnetic stirring. After the periodate addition was completed, the reaction mixture was stirred at room temperature for about an additional three hours. After the three hours, the 600 ml reaction volume had an initial specific conductivity of 9.7 mmho–cm$^{-1}$ and an initial pH of 2.5. The reaction mixture was diluted to two liters with distilled water and desalted using the hollow fiber cartridge. Washing was done using 15–18 liter of distilled water to obtain 600 ml of washed, oxidized dextran solution having a specific conductance of 10 mmho–cm-$^{-1}$ and pH of 6.7.

The solution of oxidized dextran was cooled to about 8° using an ice bath and 23.2 ml (0.275 mol) of 1,3-diaminopropane was added over about 10 minutes to the oxidized dextran solution. The resulting reaction mixture was stirred and maintained at the ice bath temperature. The formation of the yellow Schiff's base was monitored every 10–15 minutes by measuring the 335 nm absorbance of an extracted sample. In a typical experiment, the measurements at 335 nm path length cell were as shown in Table 1:

TABLE 1

| minutes | absorbance values |
|---|---|
| 0 | 0.100 |
| 5 | 2.063 |
| 15 | 2.975 |
| 30 | 3.692 |
| 45 | 3.901 |
| 60 | 4.103 |
| 75 | 3.784 |

After the absorbance had reached a plateau, 19.3 g (0.500 mol) of sodium borohydride in 19.3 ml of 1 mM aqueous potassium hydroxide was added to the reaction mixture over about 10 at ambient temperature with magnetic stirring. After the sodium borohydride addition was completed, the reaction mixture was stirred at ambient temperature for about an additional two hours. After the stirring was completed, spectroscopic measurement at 335 nm using a 1 cm path length cell gave an absorbance value of 0.067 units, which indicates that the Schiff's base compound had essentially disappeared. The reaction mixture, about 1000 ml volume, was then desalted using the hollow fiber cartridge. The initial specific conductance was 43 mmho–cm$^{-1}$ and the initial pH was 11.0. About 18–20 liters of distilled water as wash liquid were used to produce about 300 ml of 5X-aminodextran solution having a specific conductance of about 4–6 μmho–cm$^{-1}$ and a pH of 6.5–7.0. The 5X-aminodextran solution was filtered through a 0.8 μm cellulose nitrate filter and freeze dried over 48 hours, in a model TDS-00030-A, Dura-Dry® microprocessor-controlled freeze dryer (FTS Systems, Inc.) to produce 24 g (48% yield) of flaky, pale yellow crystals. Elemental analysis: C=45.83%, H=7.00%, N=4.49%, O (by difference)= 42.68%. Calculated analysis for $C_{12} H_{22}O_{8.25}N$: C=46.15%, H=7.10%, N=4.48%, O=42.26%.

The empirical formula based on actual analysis is $C_{12}H_{22}O_{8.3}N$, which is very similar to the formula $C_{12}H_{22}O_{8.25}N$ based on 6 units of glucose per one unit of fully diamine-substituted sugar ring ($C_{12}H_{28}N_4O_3$). Therefore, the degree of diamine substitution in dextran was 1/7 in contrast to a theoretical value of 1/25 based on 100% periodate cleavage and diamine substitution. Repeat experiments using 100 and 300 grams dextran produced a product having the same 1/7 degree of substitution.

Preparation of Aminodextran Coated, Functionalized-Polystyrene Latex Particles

Two types of functionalized polystyrene latex particles or beads were coated according to the invention using 5X-aminodextran as the exemplary coating material. The first type were Polybead carboxylate microspheres of 2.01 μm diameter (0.046 standard deviation) from Polysciences, Inc., Warrington, Pa., and the second type was aldehyde or aldehyde/sulfate polystyrene latex particles of 2.15 μm±5.5% diameter from IDC Corporation, Portland, Oregon. Neither of these particle types were magnetic. However, magnetic beads can be coated in the same manner and magnetic separation used instead of centrifugation to separate the beads from the suspending medium. The first step in coating the beads with 5X-aminodextran was to couple the 5X-aminodextran to particles surface functional groups by a condensation reaction between surface carboxylate or aldehyde groups and the amine groups of 5X-aminodextran.

Procedure 1

Coupling to Carboxylate Polystyrene Latex Particles

Five milliliter (5 ml) of 10 mg/ml aqueous 5X-aminodextran solution and 1 ml of 2M aqueous NaCl were added to 4 ml of aqueous suspension of 2.5% w/v solids carboxylated polystyrene latex particles. 230 µL of 10 mg/ml aqueous solution of a water soluble carbodiimide, for example, EDAC.HCl, was then added to the colloidal dispersion of latex particles and the entire mixture was mixed, preferably by means of a roller mixer, for a time in the range of about 8–16 hours.

Procedure 2

Coupling to Aldehyde/Sulfate Polystyrene Latex Particles

Five milliliters (5 ml) of 10 mg/ml aqueous 5X aminodextran and 2.619 ml of distilled water were added to 2.381 ml of aqueous suspension of 4.2% w/v solids aldehyde/sulfate polystyrene latex particles. The pH of the dispersion was then adjusted to 10.0 by the addition of 2 µl of 5M aqueous potassium hydroxide solution. The resulting mixture was then mixed, preferably by means of a roller mixer for a time in the range of about 8–16 hours.

Crosslinking of 5X-Aminodextran on Polystyrene Latex Particles

The aminodextran coated beads prepared by either Procedure 1 or 2 were washed three to four times by suspension in distilled water and centrifugation for ten (10) minutes at 3000 rpm. The beads were then resuspended in 10 ml of 2% w/v aqueous 5X-aminodextran and mixed, preferably by means of a roller mixer, for about three (3) hours. After the mixing was completed, the pH was adjusted to about 10.0 by the addition 2 µL of 5M aqueous potassium hydroxide. Immediately after the pH adjustment, 0.117 ml of 25% glutaraldehyde solution (0.311 mmoles or 1 mole per mole amino groups in 5X-aminodextran) was added to the bead containing solution and mixed therewith, preferably by roller mixing, for about one hour. The yellow color indicative of Schiff's base formation was noted after 15 minutes of mixing. The beads were then separated from free glutaraldehyde and aminodextran by centrifugation, the supernatant liquid discarded. To block unreacted aldehyde groups, the beads were resuspended in 10 ml of 1% w/v 5X-aminodextran and mixed, preferably by roller mixing, for a time in the range of about 8–16 hours. Alternatively, ethylenediamine (10 moles per mole gluteraldehyde) can be used as the blocking reagent. The Schiff's base formed by these reactions was reduced by the addition of 2.35 ml of 10 mg/ml sodium borohydride to the bead mixture and mixing for about an additional thirty minutes. Subsequently, the beads were washed four times using centrifuging and 1X PBS. The wash supernatant liquids were discarded and the washed beads were suspended in sufficient 1X PBS to give a 10 ml total volume suspension of either 5X-aminodextran coated carboxylated beads or 5X-aminodextran coated aldehyde/sulfate beads. Beads coated with 1X-, 2X- and 3X-aminodextrans may be similarly produced.

Crosslinking 3X-Aminodextran on Sulfated Polystyrene Latex Particles

Polystyrene latex particles which lack chemically reactive functional groups with which an aminodextran can bind require the use of a modified coating and crosslinking procedure. The sulfated polystyrene latex particles used in this procedure do not have the aldehyde groups which are present on aldehyde/sulfate particles.

16.7 ml of 30 mg/ml aqueous 3X-aminodextran and 77.2 ml of distilled water were added to 6.1 ml of an 8.2% w/v solid sulfated polystyrene latex particle suspension. (2.13 µm mean particle diameter IDC) in a 250 ml tissue culture flask. The pH of the resulting suspension was then adjusted to 10.0 by the dropwise addition of 0.1M aquequs sodium hydroxide (about 20 drops were used). The flask was placed on an orbital shaker and its contents mixed for about 8–16 hours. After mixing, 1.130 ml of 25% glutaraldehyde solution (3 mg glutaraldehyde per milliliter reaction volume) were added to the bead suspension which was then orbitally shaker for an additional 30 minutes. Unreacted aldehyde groups were then blocked by the addition of 2 ml of ethylenediamine (10 moles per mole glutaraldehyde), followed by further shaking for about three hours. Finally, 1 ml of aqueous 10 mg/ml sodium borohydride and 1 mM potassium hydroxide solution was added to the latex particle suspension which was then orbitally shaken for about an additional thirty minutes in order to reduce and stabilize the Schiff's base linkages. The latex particles were then separated and washed four times using centrifugation and 1X PBS respectively. The beads were resuspended in 1X PBS and the volume adjusted to make a 2.5% w/v solids suspension (final volume about 20 ml) which can be used in subsequent reactions.

Particle Activation by Sulfo-SMCC and Antibody Coupling to the 5X-Aminodextran Coated Polystyrene The conjugation of monoclonal antibodies to the aminodextran coated polystyrene latex particles was performed as described herein for gelatin coated latex particles except that 33.75 µL of 10 mg/ml Sulfo-SMCC solution was used per milliliter of 2.5% w/v solids bead suspension. The antibody conjugated, aminodextran coated polystyrene latex particles prepared according to the invention may be used in various cell population analyses by flow cytometry and other methodologies. For examples, see International Patent Application Publication WO 90/10313 and copending U.S. patent application Ser. No. 587,646, filed Sep. 29, 1990; U.S. Pat. Ser. No. 285,856 filed Dec. 16, 1988; U.S. Pat. Ser. No. 339,156 filed Apr. 14, 1989; and U.S. Pat. Ser. No. 07/525,231 filed May. 17, 1990.

Unless specified otherwise, the quantity of monoclonal antibody conjugated to beads is in the range of 3–5 mg of antibody per square meter bead surface area. The beads are prepared, for example, by the reaction of an activated antibody such as an iminothiolane activated antibody with activated beads. Typically, the reaction uses 0.625 mg of activated antibody per milliliter of 1% w/v bead suspension.

EXAMPLE 5

Polystyrene Bead T-cell Population Shift Analysis by Flow Cytometry Using Aminodextran Coated Polystyrene Latex Beads A 50 ml sample of $Na_4EDTA$-anticoagulated blood was obtained, divided among a plurality of centrifuge tubes and centrifuged at 500 g for ten (10) minutes. The majority of the plasma was removed and the residual buff colored layer of cells in each tube was pooled and further centrifuged at 500 g for an additional 10 minutes. The residual plasma and the buff colored cells were separated. Collectively, the buff colored cells and the plasma constitute the leuko-rich whole blood.

The buff colored cells were diluted with 1X PBS to obtain a plurality samples containing 4, 6, 8, 10 and $12 \times 10^5$ white blood cells (wbc), respectively, as determined on a Coulter S-Plus® counter. 100 µL aliquots of each of the 4, 6, 8, 10 and $12 \times 10^5$ wbc samples were then pipetted into a plurality of 5 ml test tubes. Subsequently, 5, 10, 15, 20, 30 and 40 µL aliquots of a suspension of T4 monoclonal antibody conjugated to 3X-aminodextran coated sulfate polystyrene latex beads (1% w/v solids, 3–5 mg antibody per square meter bead surface area and $1.786 \times 10^9$ particles per milliliter) was then pipetted into a separate tube for each of the wbc concentrations. Each tube was then nutated for two minutes.

Following nutation, 10 μL of CYTO-STAT® T4-RD1/T8-FITC dual color antibody reagent was added to each sample to enable discrimination between actual T4+ cell labelling and non-specific labelling of T-cells, i.e., T8 cells. The samples were vortexed and incubated at room temperature (range 18°–27° C.) for ten minutes. The sample tubes were then placed on a Coulter EPICS Q-Prep® (Coulter Corporation, Hialeah, Fla.) or similar instrument and processed on the thirty-five second lyse mode to lyse red blood cells (rbc). After rbcs were lysed and the samples fixed (Q-Prep), all samples were analyzed on a Coulter EPICS® Profile II flow cytometer or similar instrument. Standard programs introduced into the Profile were used to determine lymphocyte and monocyte-myeloid population as fluorescent events; in particular, those lymphocytes which are in the shifted-forward versus side-scatter region due to a change in size and/or granularity upon binding of the polystyrene latex particles.

The Profile II was calibrated with DNA-Check (Coulter Corporation, Hialeah, Fla.) beads for alignment and with Standard-Brite beads, (Coulter Corporation) for fluorescence intensity. A buff cell sample containing no polystyrene beads and no fluorescent markers was used to establish the population (quantity) of lymphocytes, monocytes and granulocytes. The lymphocyte population was Bitmapped for fluorescence analysis and all three cell type populations were boxed for cell count as fluorescent events. A buff cell sample without polystyrene beads was stained with CYTO-STAT® MsIgG1-RD1/Ms IgG1-FITC control reagent and used to set quad stats and cursors. A buff cell sample containing the dual fluorescent reagent T4-RD1/T8-FITC and no polystyrene beads was used to set color compensation. A buff cell sample containing 40 μL of T4-conjugated polystyrene latex particles was used to determine the position of the shifted cell population which was Bitmapped and boxed. A buff cell sample of T4-conjugated polystyrene latex particles was stained with MsIgG1-RD1/MsIgG1-FITC control reagent and used to set quads and cursors. A sample of T4-conjugated polystyrene latex beads with no buff cells or fluorescent reagents present was used to verify that the beads did not interfere with cells on the scattergram. Upon completion of the above steps, buff cell samples which contain the various wbc concentrations and the dual color markers (RD1 and FITC) were used to determine an original T4 cells fluorescent event count. Lastly, a buff cell sample with dual color marker and various amounts (5, 10, 15, 20, 30 and 40 μL) of the T4 containing beads of concentration 3–5 mg T4/m² bead surface area were used to determine the T4 cell fluorescent event cell.count in the region of the forward-scatter versus side-scatter plot shifted away from the remaining lymphocyte population in the direction of greater size and/or granularity.

In the preparation of the test and control samples, it is important that antibody-bead conjugates be mixed with the buff cell sample before the addition of the fluorescent markers in order to avoid saturation of antigenic sites on the T cells by the smaller and more mobile molecular dye-antibody conjugates. The T4 cell counts were estimated from the T4 fluorescent events and from S-Plus® counter versus Profile II data. [T4 events (no beads)–T4 events (40 μL beads)]×[Q-Prep Dilution Factor(11)]×[(S-Plus lymphocyte count)÷(total lymphocyte events)=1.24.] The results are summarized in Table 2 below and in FIG. 1 as the number of T4 cells shifted versus the bead-to-T4 cell ratio

TABLE 2

| WBC/100 μL (×10⁵) | T4 cells Shifted (×10⁴) | % T4 in WBC | % T4 in Lymphocytes | Bead/T4 cell (at FIG. 1 Plateau) |
|---|---|---|---|---|
| 12.0 | 18.4 | 15.3 | 39.3 | 147 |
| 10.0 | 15.3 | 15.3 | 39.3 | 234 |
| 8.0 | 11.9 | 14.9 | 38.3 | 302 |
| 6.0 | 8.80 | 14.7 | 37.8 | 603 |
| 4.0 | 6.00 | 15.0 | 38.6 | 884 |

The percentage of lymphocytes in the wbc samples was 38.9% as determined by the S-Plus® counter. The percentage of T4 cells among the lymphocytes was determined by the equation:

% T4 cells=100%×|(number of T4 cells in shifted population at plateau in plot)÷wbc count|÷0.389].

The T4 percentages were 39.3%, 39.3%, 38.3%, 37.8% and 38.6% for wbc concentrations of 12, 10, 8, 6 and 4×10⁵, respectively. The T4 percentages based on relative fluorescence events of shifted and unshifted lymphocyte population, [(T4 events (no beads)–T4 events (40 μL beads)]÷(total lymphocyte events), in forward-scatter versus side-scatter plot were 39.2, 39.5, 38.4, 38.0 and 39.0, respectively. Similar experiments with T4 monoclonal antibody conjugated to sulfate polystyrene latex beads coated with type A gelatin showed interference from shifted monocytes due to non-specific interactions with crosslinked gelatin. The use of aminodextran coated polystyrene latex beads thus provides a viable alternative when such interference is observed.

EXAMPLE 6

T4 and T8 Cell Population Analysis Using 5X-Aminodextran Coated Polystyrene Latex Particles T4 and T8 monoclonal antibodies were conjugated to 5X-aminodextran coated carboxylate polystyrene latex particles and 5X-aminodextran coated aldehyde/sulfate polystyrene latex particles. The particles were suspended in 1X PBS to give a 1% w/v mixture. A sufficiency of T4 or T8 conjugated particles was added to 200 μL whole blood. The sample volume was made up to 300 μL by the addition of 1X PBS and then vortexed for two minutes. A 100 μL aliquot was then aspirated into a Coulter VCS® (Coulter Corporation, Hialeah, Fla.) or similar instrument for analysis of the population of shifted T-cells using the methods described by T. Russell et al. in International Patent Application Publication WO 90/18013. The addition of batch lyse for red blood cells and of lyse quencher was automatically controlled by the instrument. The percent of T4 or T8 cells in the sample equals the T cell population shifted into an uncluttered region of DC versus opacity. The % T4 or T8 [(shifted T4 or T8 cell population)÷(total original lymphocyte population)]×100%. The plot from which you obtain this percentage is DC versus [(RF-85)÷DC)], where RF equals radio frequency scatter, DC equal direct current cell resistance and –85 is a constant. The quantity of monoclonal antibody conjugated, coated particles (1% w/v solids) use and the percentage T4 cells determined are shown in Table 3.

TABLE 3

A. Using Carboxylated Polystyrene Latex Particles.

| Bead Volume Used (μL) | % T4 cells |
|---|---|
| 0 | 0.00 |
| 5 | 18.94 |
| 10 | 27.61 |
| 20 | 36.76 |
| 30 | 39.30 |
| 40 | 41.17 |
| 50 | 40.84 |
| 75 | 44.07 |
| 100 | 44.13 |

B. Using Aldehyde/Sulfate Polystyrene Latex Beads.

| Volume Beads Used (μL) | % T4 cells |
|---|---|
| 5 | 28.91 |
| 10 | 29.89 |
| 20 | 34.80 |
| 30 | 38.57 |
| 40 | 39.99 |
| 50 | 40.33 |
| 75 | 42.62 |
| 100 | 44.37 |

Using either type of particles, a plateau at about 44.1–44.4% T4 cells observed when all T4 cells were shifted by an excess of polystyrene beads coated with T4 antibody. This end point value can be considered the true percentage of T4 cells among the lymphocyte population of the whole blood sample analyzed. The bead-to-T4 cell ratios at the end points were 210 and 928, respectively.

Coupling of 1X-aminodextran to Tosyl-Activated Polystyrene Magnetite-Containing Particles (No Crosslinking)

2 ml of 30 g/ml uniform, porous polystyrene particles having embedded magnetic material (M-450 Dynabeads®, tosyl activated, 4.4 μm±5%; Dynal, Incorporated) were washed three times with 0.25M borate buffer, pH 9.8. 0.198 ml of 45.4 mg/ml 1X-aminodextran was added to the washed beads and the total volume was adjusted to 2.4 ml with the borate buffer to give a 2.5% w/v solids suspension having an 1X-aminodextran concentration of 3.75 mg/ml. The suspension was the mixed for about 8–16 hours. The particles were then magnetically separated, washed four times with 2.4 ml of 1X PBS and resuspended in 1X PBS to give a particle suspension of total volume 2.4 ml.

T11 monoclonal antibody was conjugated to the 1X-aminodextran coated M-450 beads using the method described herein for conjugating monoclonal antibodies to gelatin coated ferrite particles. The antibody conjugated particles were then used in a T11/B4 lymphoid cell assay performed using the method of Example 1. The results are summarized in Table 4 for samples treated with 0, 25, 50 and 100 μL of T11 antibody-conjugated M-450 particles. The results indicate there was no significant non-specific removal of B cells. The bead-to-cell ratio was 48:1 when 100 μL of particles were used.

TABLE 4

| μL T11 Beads Used | T11+ Count | B4+ Count |
|---|---|---|
| 0 (Control) | 18,470 | 2,643 |
| 25 | 1,680 | 2,709 |
| 50 | 1,348 | 2,999 |
| 100 | 291 | 2,675 |

Coupling 5X-Aminodextran to Polystyrene-Magnetite Particles 50 ml of polystyrene-magnetite particles (10% w/v solids in 0.5% SDS, 0.980 μm means diameter, —COOH functional group, 23.1% magnetite) were added to a reaction flask containing 150 ml of 1% sodium azide, 10 mM sodium bicarbonate solution. The contents were mixed for about 8–16 hours using shaker and the particles then twice magnetically separated and washed using 200 mL of the 10 mM aqueous sodium bicarbonate. The washed particles were then suspended in 0.2M aqueous sodium chloride and the suspension volumed adjusted to about 150 ml. A solution of 750 mg 5X-aminodextran in about 10 ml of 0.2M aqueous sodium chloride was prepared and added to the particle suspension. The total volume was then adjusted to 200 ml with 0.2M aqueous sodium chloride to give a 2.5% w/v solids suspension having a 5X-aminodextran concentration of 3.75 mg/ml. A 1.80 ml sample of 10 mg/ml EDAC in 0.2M aqueous sodium chloride was then added to the particle suspension to facilitate coupline aminodextran amine groups with the —COOH group present on the particle's surface. The EDAC containing suspension was mixed on the orbital shaker for about 8–16 hours and then magnetically separated and washed three times with distilled water. The washed 5X-aminodextran coated beads were then resuspended in sufficient 1X PBS to yield 200 mL of 2.5% w/v solids suspension.

Activation of 5X-Aminodextran-Coated Polystyrene-Magnetic Particles by Sulfo-SMCC Except for the following differences, monoclonal antibodies were conjugated to-the 5X-aminodextran-coated polystyrene-magnetite particles by the procedures described herein for conjugating monoclonal antibodies to gelatin coated particle.

1. Activation of the 5X-aminodextran coated particles was done using 33.75 μL of 10 mg/ml sulfo-SMCC solution per milliliter of 2.5% w/v solids suspension.
2. Antibody-particle coupling was done using about 0.313 mg iminothiolane-activated monoclonal antibody per milliter of 1.25% w/v solids suspension of activated particles.

The activation of beads by iminothiolane and antibodies by sulfo-SMCC may be reversed or other reagents used as activating as specified elsewhere herein.

EXAMPLE 7

Test Results Summary for Antibodies Conjugated to 5X-Aminodextran Coated Particles The following assay results were obtained using the protocols described in Examples 1–3.

A. Erythrocyte/Thrombocyte Assay

An erythrocyte/thrombocyte assay was performed using 0–250 μL of 0.8333% w/v solids, KC-16 conjugated magnetic beads. The results are summarized in Table 5. The results indicate that 100 μL of 0.833% w/v beads contains $1.32 \times 10^9$ particles which remove $4.9 \times 10^7$ rbcs from assay sample, thus yielding a bead-to-cell ratio of 27.

TABLE 5

RBC Depletion Using Magnetic Beads

| μL Beads Used | wbc × $10^4$ | rbc × $10^7$ | platelets × $10^6$ |
|---|---|---|---|
| 0 | 7.0 | 4.9 | 2.5 |
| 5 | 5.0 | 4.3 | 2.1 |
| 10 | 6.0 | 3.9 | 1.8 |
| 20 | 6.0 | 3.0 | 1.6 |

TABLE 5-continued

RBC Depletion Using Magnetic Beads

| μL Beads Used | wbc × $10^4$ | rbc × $10^7$ | platelets × $10^6$ |
|---|---|---|---|
| 40 | 6.0 | 1.1 | 1.6 |
| 60 | 6.0 | 0.5 | 2.2 |
| 80 | 6.0 | 0.2 | 2.2 |
| 100 | 6.0 | <0.1 | 2.2 |
| 150 | 6.0 | <0.1 | 2.0 |
| 200 | 6.0 | <0.1 | 2.1 |
| 250 | 5.0 | <0.1 | 2.2 |

B. T4/T8 Lymphoid Cell Assay

A T4/T8 lymphoid depletion assay was carried out using 0–250 μL of 0.025% w/v solids, T4 monoclonal antibody conjugated magnetic beads. The results are summarized in Table 6. After scaling the total lymphocyte fluorescent events to the number of lymphocytes measured on a Coulter S-plus® Counter, the number of T4 cells remaining after each depletion was estimated and these data were used to show that 150 μL of 0.25% w/v solids beads contains $6.0 \times 10^7$ particles which removed $6.0 \times 10$ 5T4 cells, thereby yielding a bead-to-cell ratio of 100.

TABLE 6

| μL Beads Used | T4 | T8 |
|---|---|---|
| 0 | 40,920 | 26,278 |
| 5 | 30,058 | 24,169 |
| 10 | 25,920 | 23,097 |
| 30 | 21,238 | 22,467 |
| 40 | 8,630 | 23,183 |
| 60 | 2,990 | 22,384 |
| 80 | 1,985 | 22,482 |
| 100 | 1,096 | 22,482 |
| 150 | 108 | 22,680 |
| 200 | 40 | 22,816 |
| 250 | 16 | 22,627 |

C. Erythrocyte/Thrombocyte Assay

An erythrocyte/thrombocyte assay was performed using 0–250 μL of 0.25% w/v solids, PLT-1 monoclonal antibody conjugated magnetic beads. The results are summarized in Table 7. The results indicate that 200 μL of 0.25% w/v solids beads contains $7.92 \times 10^8$ particles which removed $9.2 \times 10^6$ platelets, thereby yielding a bead-to-platelet ratio of 8.6.

TABLE 7

Platelet Depletion Using Magnetic Beads

| μL Beads Used | wbc × $10^5$ | rbc × $10^7$ | platelets × $10^6$ |
|---|---|---|---|
| 0 | 2.3 | 5.3 | 9.2 |
| 5 | 2.3 | 5.3 | 7.7 |
| 10 | 2.3 | 5.3 | 7.0 |
| 20 | 2.3 | 5.3 | 5.5 |
| 40 | 2.2 | 5.3 | 3.4 |
| 60 | 2.3 | 5.3. | 1.7 |
| 80 | 2.2 | 5.3 | 1.0 |
| 100 | 2.2 | 5.3 | 0.4 |
| 150 | 2.2 | 5.3 | 0.1 |
| 200 | 2.2 | 5.4 | <0.1 |
| 250 | 2.2 | 5.1 | <0.1 |

D. Myeloid Cell Assay

A myeloid cell assay was performed using 0–250 μL of 0.125% w/v, M02 monoclonal antibody conjugated magnetic beads. The results are summarized in Table 8. The results indicated that 200 μL of 0.125% w/v solids beads contains $4.0 \times 10^8$ particles which were estimated to remove $4.8 \times 10^4$ monocytes, thereby yielding a bead-to-monocyte ratio of $8.3 \times 10^3$.

TABLE 8

Monocyte Cell Depletion Using Magnetic Beads

| | Counts | | |
|---|---|---|---|
| μL Beads Used | Lymphocytes | Monocytes | Granulocytes |
| 0 | 78,931 | 5,958 | 118,649 |
| 5 | 78,318 | 4,297 | 117,991 |
| 10 | 78,836 | 4,128 | 118,943 |
| 20 | 76,447 | 3,978 | 118,642 |
| 40 | 76,386 | 2,308 | 121,560 |
| 60 | 74,597 | 1,700 | 121,831 |
| 80 | 75,069 | 1,013 | 118,895 |
| 100 | 76,837 | 800 | 117,794 |
| 150 | 76,613 | 368 | 116,520 |
| 200 | 78,018 | 214 | 118,762 |
| 250 | 78,817 | 228 | 119,026 |

E. Myeloid Cell Assay

A myeloid cell assay was performed using 0–250 μL of 0.1% w/v solids, KC-48 monoclonal antibody conjugated magnetic beads. The results are summarized in Table 9. The results indicate that 150 μL of 0.1% w/v solids beads contains $2.4 \times 10^8$ particles which were estimated to remove $1.6 \times 10^6$ granulocytes, thereby yielding a bead-to-granulocyte ratio of 149.

TABLE 9

Granulocyte Cell Depletion Using Magnetic Beads

| | Counts | | |
|---|---|---|---|
| μL Beads Used | Lymphocytes | Monocytes | Granulocytes |
| 0 | 92,098 | 11,028 | 81,738 |
| 10 | 91,543 | 7,001 | 9,653 |
| 50 | 88,791 | 5,856 | 2,547 |
| 100 | 88,669 | 5,717 | 1,849 |
| 150 | 88,924 | 5,948 | 1,409 |
| 200 | 89,738 | 5,697 | 1,316 |
| 250 | 81,183 | 5,029 | 1,316 |

A similar depletion study was conducted using the same control samples as Table 9 and 0–250 μL of 0.5% w/v solids, 1D3 monoclonal antibody conjugated magnetic beads. These results are summarized in Table 10. The results indicate that 50 μL of 0.5% w/v solids beads contains $4.0 \times 10^8$ particles which were estimated to remove $1.54 \times 10^6$ neutrophils, thereby giving a bead-to-neutrophil ratio of 260.

TABLE 10

Neutrophil cell Depletion Using Magnetic Beads

| | Counts | | |
|---|---|---|---|
| μL Beads Used | lymphocytes | monocytes | granulocytes |
| 0 | 92,098 | 11,028 | 81,738 |
| 10 | 87,708 | 8,617 | 7,084 |
| 50 | 87,288 | 7,306 | 4,688 |
| 100 | 89,300 | 7,717 | 4,952 |
| 150 | 80,257 | 7,468 | 3,896 |
| 200 | 79,666 | 6,185 | 4,691 |
| 250 | 75,726 | 5,070 | 4,529 |

F. T11/B4 Lymphoid Cell Assay

A T11/B4 lymphoid cell assay was performed using 0–60 μL of 0.25% w/v solids, T11 monoclonal antibody conjugated magnetic beads. The results are summarized in Table 11. The results indicate that 20 μL of 0.25% w/v solids beads contains $8.0 \times 10^7$ particles which were estimated to remove $6.46 \times 0.25$ T11+ cells, thereby yielding a bead-to-T11+ cell ratio of 124.

TABLE 11

T11+ Cell depletion Using Magnetic Beads

| μL Beads Used | Counts | | | |
|---|---|---|---|---|
| | T11+ | B4+ | Monocytes | Granulocytes |
| 0 | 40,112 | 7,728 | 14,569 | 62,540 |
| 5 | 17,919 | 8,352 | 10,227 | 82,620 |
| 10 | 8,789 | 8,160 | 5,974 | 62,268 |
| 20 | 791 | 7,801 | 5,568 | 69,571 |
| 40 | 622 | 7,846 | 4,088 | 63,587 |
| 60 | 429 | 7,550 | 2,812 | 57,175 |

A second depletion study was performed using the same control sample as used in Table 11 and samples depleted using 5–60 μL of 0.25% w/v solids, B4 monoclonal antibody conjugated magnetic beads. The results are summarized in Table 12. The results indicate that 40 μL of 0.25% w/v solids beads contain $1.6 \times 10^8$ particles which were estimated to remove $1.23 \times 10^5$ B4+cells, thereby yielding a bead-to-B4+ cell ratio of 1300.

TABLE 12

B4+ Cell Depletion Using Magnetic Beads

| μL Beads Used | Counts | | | |
|---|---|---|---|---|
| | T11+ | B4 | Monocytes | Granulocytes |
| 0 | 40,112 | 7,728 | 14,569 | 62,540 |
| 5 | 37,103 | 5,618 | 7,523 | 66,430 |
| 10 | 33,754 | 2,587 | 8,158 | 65,198 |
| 20 | 33,393 | 888 | 7,656 | 59,380 |
| 40 | 33,473 | 131 | 8,846 | 64,326 |
| 60 | 32,956 | 43 | 5,557 | 52,345 |

G. Myeloid Cell Assay Using Magnetic Beads

A myeloid cell depletion assay of wbcs was performed using 0–250 μL of 0.5% w/v solids, KC-56 monoclonal antibody conjugated magnetic beads. The results are summarized in Table 13. The results indicate that 250 μL of beads contains $1.98 \times 10^9$ particles which were estimated to remove $1.35 \times 10^6$ wbcs, thereby yielding a bead-to-wbc ratio of 1470.

TABLE 13

WBC Depletion

| μL Beads Used | Counts | | |
|---|---|---|---|
| | Lymphocytes | Monocytes | Granulocytes |
| 0 | 50,616 | 10,238 | 24,526 |
| 5 | 26,574 | 4,962 | 36,066 |
| 10 | 12,922 | 2,821 | 32,079 |
| 20 | 4,967 | 2,031 | 30,468 |
| 40 | 1,724 | 1,017 | 22,529 |
| 60 | 671 | 630 | 16,670 |
| 80 | 473 | 450 | 13,167 |
| 100 | 343 | 304 | 11,456 |
| 150 | 144 | 185 | 7,446 |
| 200 | 75 | 102 | 5,474 |
| 250 | 5 | 1 | 65 |

We claim:

1. A process for the preparation of colloidal particles having (A) a hydrophobic non-gelatin, non-aminodextran polymeric core coated with a substance selected from the group consisting of type A, acid cured gelatin of Bloom in the range 60 to 300 and an aminodextran having a molecular weight in the range of 10,000 to 2 million, and (B) a plurality of functional groups pendent from said gelatin or aminodextran coating, said process comprising:

(a) coating said gelatin or aminodextran onto the surface of a polymeric core selected from the group consisting of a polymeric substance having amine-reactive functional groups and a polymeric core not having amine-reactive functional groups, said coating being by the method of:
      (i) adsorbing said gelatin or aminodextran onto the surface of said core or
      (ii) convalently coupling said aminodextran to said core by reaction of aminodextran amine groups and said amine-reactive groups present on said core;

(b) (i) crosslinking the gelatin or aminodextran coating of step (a) (i) by reaction of said coating with a chemical crosslinking agent, or
      (ii) selectively crosslinking or not crosslinking the aminodextran coating of step (a) (ii), said crosslinking being by reaction of said coating with a chemical crosslinking agent;

(c) blocking free, unreacted crosslinking agent functional groups present on the surface of any step (b) crosslinked product by reaction of said groups with a polyamine such that at least one polyamine —$NH_2$ group reacts with the unreacted crosslinking agent functional groups and at least one polyamine —$NH_2$ group remains unreacted; and (d) washing the particles of step (c) or the uncrosslinked particles of step (b) (ii) to obtain colloidal particles having a solid polymer core coated with gelatin or aminodextran and having pendent amine groups.

2. The process in accordance with claim 1 wherein said core is in the size range of about 0.1 to 5.0 microns.

3. The process in accordance with claim 1 wherein said core is in the size range of about 0.1 to 1.0 microns.

4. The process in accordance with claim 1 wherein the polymeric core is magnetic.

5. Particles in accordance with claim 1, 2, 3 or 4 wherein said polymeric substance is polystyrene latex.

6. The process in accordance with claim 5 wherein said coating is selected from the group consisting of 1X-, 2X-, 3X- and 5X-aminodextran.

7. The process in accordance with claim 5 wherein said coating is 5X-aminodextran.

8. The process in accordance with claim 5 wherein the product of step (d) is derivatized to have pendent functional groups selected from the group consisting of maleimidyl groups, sulfhydryl groups, polyclonal antibodies, monoclonal antibodies and biological cells.

9. The process in accordance with claim 5 wherein said polyamine is selected from the group consisting of ethylenediamine, 1,3-diaminopropane, 1,4-cyclohexanediamine, 1,4-cyclohexenediamine, 1,4-phenylenediamine, diethylene-triamine and aminodextrans.

* * * * *